US008778648B2

(12) United States Patent
Anderson et al.

(10) Patent No.: US 8,778,648 B2
(45) Date of Patent: *Jul. 15, 2014

(54) ENZYMES FOR REDUCED IMMUNOLOGICAL STRESS

(75) Inventors: David M. Anderson, Rockville, MD (US); Humg-Yu Hsiao, Rockville, MD (US); Lin Liu, Rockville, MD (US)

(73) Assignee: Eli Lilly and Company, Indianapolis, IN (US)

(*) Notice: Subject to any disclaimer, the term of this patent is extended or adjusted under 35 U.S.C. 154(b) by 488 days.

This patent is subject to a terminal disclaimer.

(21) Appl. No.: 13/072,123

(22) Filed: Mar. 25, 2011

(65) Prior Publication Data

US 2011/0171345 A1  Jul. 14, 2011

Related U.S. Application Data

(62) Division of application No. 11/610,572, filed on Dec. 14, 2006, now Pat. No. 7,914,782.

(60) Provisional application No. 60/750,339, filed on Dec. 15, 2005.

(51) Int. Cl.
| C12N 9/00 | (2006.01) |
| A61K 38/47 | (2006.01) |
| C12N 9/24 | (2006.01) |

(52) U.S. Cl.
CPC .............. *C12N 9/2488* (2013.01); *A61K 38/47* (2013.01)
USPC .......................................... 435/183; 435/200

(58) Field of Classification Search
None
See application file for complete search history.

(56) References Cited

U.S. PATENT DOCUMENTS

| 5,807,694 | A | * | 9/1998 | Zawistowski | 435/7.35 |
| 5,989,600 | A | | 11/1999 | Nielsen et al. | |
| 6,022,566 | A | | 2/2000 | Miller | |
| 6,162,473 | A | * | 12/2000 | Fodge et al. | 426/53 |
| 6,183,739 | B1 | | 2/2001 | Beudeker et al. | |
| 6,284,509 | B1 | | 9/2001 | Ferrer et al. | |
| 6,290,952 | B1 | | 9/2001 | Poelstra et al. | |
| 6,331,426 | B1 | | 12/2001 | Bjornvad et al. | |
| 6,383,485 | B1 | | 5/2002 | Cook | |
| 6,500,658 | B1 | | 12/2002 | Wu et al. | |
| 6,558,693 | B1 | | 5/2003 | Knap et al. | |
| 6,562,340 | B1 | | 5/2003 | Bedford et al. | |
| 6,780,628 | B2 | * | 8/2004 | Anderson et al. | 435/198 |
| 2002/0146399 | A1 | | 10/2002 | Raczek | |
| 2004/0126459 | A1 | | 7/2004 | Raczek | |
| 2005/0118152 | A1 | | 6/2005 | De Simone | |
| 2009/0010912 | A1 | | 1/2009 | Brands et al. | |
| 2010/0022617 | A1 | | 1/2010 | Kiss | |
| 2011/0171345 | A1 | | 7/2011 | Anderson et al. | |
| 2011/0177195 | A1 | | 7/2011 | Anderson et al. | |

FOREIGN PATENT DOCUMENTS

| GB | 2 261 877 | 6/1993 |
| JP | 58-201949 A | 11/1983 |
| WO | 95/28850 | 11/1995 |
| WO | WO 97/41739 | 11/1997 |
| WO | WO 98/20750 | 5/1998 |
| WO | WO 99/03497 | 1/1999 |
| WO | WO 01/41785 | 12/2000 |
| WO | WO-02057048 A2 | 7/2002 |
| WO | WO 03/062409 A2 | 7/2003 |
| WO | WO 2004/054609 A1 | 7/2004 |
| WO | WO 2005/074978 A1 | 8/2005 |
| WO | WO 2005094874 A1 * | 10/2005 |

OTHER PUBLICATIONS

Nakajima, T., Maitra, S.K., and Ballou, C.E. "An endo-alpha1 leads to 6-D-mannanase from a soil bacterium. Purification, properties, and mode of action", Journal of Biological Chemistry 1976, vol. 251, pp. 174-181.*
Rippie, E.G. In Remington's Pharmaceutical Sciences, 17th Ed., Chapter 89, Gennaro, et al., Ed.; Mack Publishing Company: Easton, PA, 1985; pp. 1585-1602.*
Office Action mailed Jun. 1, 2011 issued in Australian Application No. 2006329927.
Notice of Acceptance mailed Sep. 15, 2011 issued in Australian Application No. 2006329927.
Examination Report mailed Sep. 30, 2010 issued in New Zealand Application 569,186.
Examination Report and Notice of Acceptance mailed Aug. 17, 2011 issued in New Zealand Application 569,186.
Second Office Action issued Jun. 13, 2013 in Chinese Application 201110196871.1 (w/ translation).
First Office Action issued Jul. 20, 2012 in Chinese Application 201110196871.1 (w/ translation).
Office Action mailed Jan. 17, 2013 issued in Canadian Application No. 2,633,066.
Office Action mailed Apr. 23, 2013 in Korean Patent Application No. 10-2008-7017119 (w/ translation).
Minutes of Oral Proceedings mailed May 7, 2010 in European Application No. 06848883.2.
European Office Action mailed Mar. 4, 2009, in European Application No. 06848883.2.
European Office Action mailed Oct. 13, 2008, in European Application No. 06848883.2.
Holt et al., "Comparison of the Effects of Infection with *Salmonella enteritidis*, in Combination with an Induced Molt, on Serum Levels of the Acute Phase Protein, $\alpha_1$, Acid Glycoprotein, in Hens," Poultry Science, 2002, pp. 1295-1300, vol. 81.
Hornung et al., 5'-Triphosphate RNA Is the Ligand for RIG-1, Science, Nov. 2006, pp. 994-997, vol. 314.

(Continued)

*Primary Examiner* — Allison Ford
*Assistant Examiner* — Michelle F Paguio Frising
(74) *Attorney, Agent, or Firm* — Drinker Biddle & Reath LLP

(57) ABSTRACT

Compositions suitable for oral administration to an animal comprising at least one immune stress-reducing enzyme in an amount effective to decrease the level of positive acute phase protein in an animal, increase the level of negative acute phase protein in an animal, and/or improve animal growth performance is provided, as are methods using such compositions. The compositions include animal feed compositions, liquid compositions other than animal feed, and solid compositions other than animal feed.

16 Claims, 4 Drawing Sheets

(56) References Cited

OTHER PUBLICATIONS

Ogawa et al., "α-Subunit of β-Conglycinin, an Allergenic Protein Recognized by IgE Antibodies of Soybean-sensitive Patients with Atopic Dermatitis," Biosci. Biotech. Biochem., 1995, pp. 831-833, vol. 59, No. 5.
Daskiran, M., "An Evaluation of Endo-β-D-mannanase (Hemicell) Effects on Broiler Performance and Energy Use in Diets Varying in β-Mannan Content," Poultry Science, 83(4):662-668 (2004).
Lee, J.T., et al., "Effects of Guar Meal By-Product with and Without β-Mannanase Hemicell on Broiler Performance," Poultry Science, 84(8):1261-1267 (Aug. 2005).
Notice of Allowance issued on Nov. 30, 2010 in U.S. Appl. No. 11/610,572.
Office Action issued on Jun. 14, 2010 in U.S. Appl. No. 11/610,572.
Office Action issued on Nov. 30, 2009 in U.S. Appl. No. 11/610,572.
Office Action issued on May 26, 2009 in U.S. Appl. No. 11/610,572.
Adachi et al., "Characterization of β-Glucan Recognition Site on C-Type Lectin, Dectin 1," Infection and Immunity, vol. 72, No. 7, pp. 4159-4171, Jul. 2004.
American Academy of Pediatrics, Committee on Nutrition, "Soy Protein-based Formulas: Recommendations for Use in Infant Feeding," Pediatrics, Jan. 1998, pp. 148-153, vol. 101, No. 1.
Baumgarth et al., "Inherent specificities in natural antibodies: a key to immune defense against pathogen invasion," Springer Semin Immun, 2005, pp. 347-362, vol. 26.
Bell et al., "The molecular structure of the Toll-like receptor 3 ligand-binding domain," PNAS, Aug. 2005, pp. 10976-10980, vol. 102, No. 31.
Blach-Olszewska Z., "Innate immunity: cells, receptors, and signaling pathways," Arch Immunol Ther Exp, 2005, pp. 245-253, vol. 53.
Bruni et al., "Different Effect of Statins on Platelet Oxidized-LDL Receptor (CD36 and LOX-1) Expression in Hypercholesterolemic Subjects," Clin Appl Thrombosis/Hemostasis, 2005, pp. 417-428, vol. 11, No. 4.
Burks et al., "Enzyme-Linked Immunosorbent Assay and Immunoblotting Determination of antibody Response to Major Component Proteins of Soybeans in Patients with Soy Protein Intolerance," J Pediatric Gastroenterology and Nutrition, 1989, pp. 195-203, vol. 8, No. 2.
Chimini G., "Engulfing by lipids: a matter of taste?" Cell Death and Differentiation, 2001, pp. 545-548, vol. 8.
Fabrick et al., "Innate Immunity in a Pyralid Moth," J. Biological Chemistry, Jun. 2004, pp. 26605-26611, vol. 279, No. 25.
Ferrer, "Revisiting the Cellulosimicrobium cellulans yeast-lytic β-1,3-glucanases toolbox: A review," Microbial Cell Factories, vol. 5, No. 10, published online Mar. 17, 2006.
Fleckenstein et al., "Interaction of an Outer Membrane Protein of Enterotoxigenic Escherichia coli with Cell Surface Heparan Sulfate Proteoglycans," Infection and Immunity, vol. 70, No. 3, pp. 1530-1537, Mar. 2002.
Fournier et al., "Recognition of Staphylococcus aureus by the Innate Immune System," Clinical Microbiology Reviews, Jul. 2005, pp. 521-540, vol. 18, No. 3.
Fukumoto et al., "Critical Roles of CXC Chemokine Ligand 16/Scavenger Receptor that Binds Phosphatidylserine and Oxidized Lipoprotein in the Pathogenesis of Both Acute and Adoptive Transfer Experimental Autoimmune Encephalomyelitis," J Immunol, 2004, pp. 1620-1627.
Hacker et al., "Immune Cell Activation by Bacterial CpG-DNA through Myeloid Differentiation Marker 88 and Tumor Necrosis Factor Receptor-Associated Factor (TRAF) 6," J. Exp. Med., vol. 192, No. 4, pp. 595-600, Aug. 21, 2000.
Hansen et al., "CL-46, a Novel Collectin Highly Expressed in Bovine Thymus and Liver," J Immun, 2002, pp. 5726-5734.
Haurum et al., "Studies on the carbohydrate-binding characteristics of human pulmonary surfactant-associated protein A and comparison with two other collectins: mannan-binding protein and conglutinin," Biochem. J., vol. 393, pp. 873-878, 1993.
Holt et al., "Comparison of the Effects of Infection with Salmonella enteritidis, in Combination with an Induced Molt, on Serum Levels of the Acute Phase Protein, $\alpha_1$ Acid Glycoprotein, in Hens," Poultry Science, 2002, pp. 1295-1300, vol. 81.
Honko et al., "Effects of Flagellin on Innate and Adaptive Immunity," Immunologic Research, vol. 33, No. 1, pp. 83-101, 2005.
Hornung et al., 5'-Triphosphate RNA Is the Ligand for RIG-1, Science, Nov. 2006, pp. 994-997, vol. 314.
Huang et al., "Th1-Like cytokine Induction by Heat-Killed Brucella abortus Is Dependent on Triggering of TLR9," J Immunol, 2005, pp. 3964-3970.
Hultén et al., "Interleukin 6, serum amyloid a and haptoglobin as markers of treatment efficacy in pigs experimentally infected with Actinobacillus pleuropneumoniae," Veterinary Microbiology, 2003, pp. 75-89, vol. 95.
Jameson et al., "γδ T cell-induced hyaluronan production by epithelial cells regulates inflammation," Jem, Apr. 2005, pp. 1269-1279, vol. 201, No. 8.
Klabunde et al., "Recognition of Plasmodium falciparum proteins by mannan-binding lectin, a component of the human innate immune system," Parasitol Res, 2002, pp. 113-117, vol. 88.
Lynch et al., "L-Ficolin Specifically Binds to Lipoteichoic Acid, a Cell Wall Constituent of Gram-Positive Bacteria, and Activates the Lectin Pathway of Complement," J Immunol, 2004, pp. 1198-1202.
Meiss et al., "Biochemical characterization of Anabaena sp. Strain PCC 7120 non-specific nuclease NucA and its inhibitor Nui A," Eur. J. Biochem., vol. 251, No. 3, pp. 924-934, 1998.
Murata et al., "Current research on acute phase proteins in veterinary diagnosis: an overview," The Veterinary Journal, 2004, pp. 28-40, vol. 168.
Mushtaq et al., "Prevention and Cure of Systemic Escherichia coli K1 Infection by Modification of the Bacterial Phenotype," Antimicrobial Agents and Chemotherapy, vol. 48, No. 5, pp. 1503-1508, May 2004.
Nonnenmacher et al., "DNA from Periodontopathogenic Bacteria Is Immunostimulatory for Mouse and Human Immune Cells," Infection and Immunity, Feb. 2003, pp. 850-856, vol. 71, No. 2.
Ogawa et al., "α-Subunit off β-Conglycinin, an Allergenic Protein Recognized by IgE Antibodies of Soybean-sensitive Patients with Atopic Dermatitis," Biosci. Biotech. Biochem., 1995, pp. 831-833, vol. 59, No. 5.
Peiser et al., "Scavenger receptors to innate immunity," Current Opinion in Immunology, vol. 14, pp. 123-128, 2002.
Rice et al., "Human monocyte scavenger receptors are pattern recognition receptors for (1→3)-β-D-glucans," J Leukocyte Biology, Jul. 2002, pp. 140-146, vol. 72.
Schlegel et al., "Phosphatidylserine, a death knell," Cell Death and Differentiation, 2001, pp. 551-563, vol. 8.
Schulze E., "Zur Chemie der pflanzlichen Zellmembranen," Physiol. Chem., vol. 16, pp. 387-438, 1892.
Schulze, "Zur Kenntniss der chemischen Zusammen-setzung der pflanzlichen Zellmembranen," Berichte der Deutschen Botanischen Gessellschaf, vol. 24, pp. 2277-2287, 1891.
Takahashi et al., "Lack of mannose-binding lectin-A enhances survival in a mouse model of acute septic peritonitis," Microbes and Infection, 2002, pp. 773-784, vol. 4.
Thompson et al., "Identification and Characterization of a Chitinase Antigen from Pseudomonas aeruginosa Strain 385," Applied and Environmental Microbiology, vol. 67, No. 9, pp. 4001-4008, Sep. 2001.
Tosi, M.F., "Innate immune responses to infection," J Allergy Clin Immunol, Aug. 2005, pp. 241-249, vol. 116, No. 2.
Van Uden et al., "Immunostimulatory DNA and applications to allergic disease," Molecular mechanisms in allergy and clinical immunology, J Allergy Clin Immunol, Nov. 1999, pp. 902-910.
Whistler et al., "Hemicelluloses,"Polysaccharide Chemistry, Chapter IV, 112, Academic Press, pp. 112-133, 1953.
Partial European Search Report issued on Oct. 21, 2010 in application No. EP 10 16 1087.
Debus et al., "Does Cortisol Mediate Endotoxin-Induced Inhibition of Pulsatile Luteinizing Hormone and Gonadotropin-Releasing Hormone Secretion?," Endocrinology, vol. 143, No. 10, pp. 3748-3788, 2002.

(56) References Cited

OTHER PUBLICATIONS

Walsh et al., "Technical Note: Detection and Quantification of Supplemental Fungal B-Glycanase Activity in Animal Feed," *J. Anim. Sci.*, pp. 1074-1076, 1995.

Liu et al., "Versatility takes enzymes beyond simple blending," *Feed Tech*, www.AgriWorld.nl, pp. 25-27, 2003.

European Commission, "Report of the Scientific Committee on Animal Nutrition on the Safety of Product: Rovabio Excel for Piglets," *Health & Consumer Protection Directorate-General—Directorate C—Scientific Opinions*, 4 pgs., Mar. 27, 2003.

Vranjes et al., "Influence of Trichoderma viride enzyme complex on Nutrient Utilization and Performance of Laying Hens in diets with and without Antibiotic Supplementation," *Poultry Sci.*, vol. 75, pp. 551-555, 1996.

Notice of Allowance issued on Nov. 30, 2010 by the Examiner in U.S. Appl. No. 11/610,572 (US 2007-0141041).

Office Action issued on Jun. 14, 2010 by the Examiner in U.S. Appl. No. 11/610,572 (US 20071-0141041).

Office Action issued on Nov. 30, 2009 by the Examiner in U.S. Appl. No. 11/610,572 (US 2007-0141041).

Office Action issued on May 26, 2009 by the Examiner in U.S. Appl. No. 11/610,572 (US 2007-0141041).

\* cited by examiner

ENZYMES FOR REDUCED IMMUNOLOGICAL STRESS

CROSS REFERENCE TO RELATED APPLICATIONS

The present application is a divisional of U.S. application Ser. No. 11/610,572, filed Dec. 14, 2006, now U.S. Pat. No. 7,914,782 which claims the benefit under 35 U.S.C. §119(e) of the filing date of U.S. Provisional Application No. 60/750,339, filed Dec. 15, 2005, the entire contents of which are incorporated herein by reference.

FIELD OF THE INVENTION

The present invention provides compositions and methods for reducing immunological stress and improving animal growth performance. In particular, the invention provides compositions comprising enzymes that are effective to reduce immunological stress or that are effective to treat or prevent infection or that are effective to improve animal growth performance. The invention also provides methods using the compositions.

BACKGROUND

An animal may experience immunological stress for a number of reasons, including exposure to an antigen that is recognized by the animal's immune system. An antigen may trigger an immune response that is an adaptive immune response or that is an innate immune response. When an immune response is triggered, the animal experiences immunological stress as its immune system responds to the perceived threat. Often, immunological stress hampers animal growth performance.

Acute phase proteins (APP) are a group of blood proteins whose blood concentration changes when an animal is experiencing stress, such as infection, inflammation, surgical trauma, or other internal or external challenges. See, e.g., Murata et al., *Vet. J.* 168: 28 (2004). APP are believed to play a role in an animal's innate immune response. For example, APP may be involved in restoring homeostasis and restraining microbial growth until an acquired immunity is developed.

APP include "negative" proteins whose concentration decreases with stress, and "positive" proteins whose concentration increases with stress. See, e.g., Murata et al., supra. Negative APP include albumin and transferrin. Positive APP include proteins synthesized by hepatocytes upon stimulation by pro-inflammatory cytokines and released into the bloodstream, such as haptoglobin, C-reactive protein, serum amyloid A, ceruloplasmin, fibrinogen, and α-1-acid glycoprotein (AGP). Extra-hepatic production of APP also has been reported for most mammalian species. Id. Pro-inflammatory cytokines such as interleukin-6 (IL-6) and tumor necrosis factor α (TNF-α) are believed to be the major mediators of APP synthesis in the liver. Inflammation, infection or tissue injury triggers cytokine release by defense-oriented cells, thereby inducing APP synthesis. The induction of positive APP also is associated with a decrease in the synthesis of negative APP. Id.

Methods of quantifying APP have been established, and circulating APP concentration (e.g., serum levels of APP) has been correlated to the severity of the animal's condition. Id. Thus, APP concentration can be used as an indicator of an animal's immune stress level.

An animal's immune system may recognize antigens that do not pose a real threat to the animal's health, such as plant- and animal-derived ingredients in animal feed compositions. These antigens may trigger an immune response, such as an innate immune response, thereby causing the animal to experience immunological stress. This stress response can be identified and monitored via serum APP concentration.

Even when the immune-triggering antigen did not pose a real threat to the animal's health, the stress response can have a detrimental effect. This may be observed as a decrease in feed efficiency, a decrease in weight gain rate or decrease in weight, an increase in susceptibility to infection, or an increase in body temperature, for example.

The use of antibodies, such as anti-phospholipase A2 antibodies, to reduce gastrointestinal inflammation in animals has been described. See, e.g., U.S. Pat. No. 6,383,485. Feed compositions have been described that comprise a hemicellulase capable of degrading β-mannan-containing hemicellulose (e.g., a β-mannanase-type hemicellulase), such as endo-1,4-β-mannanase, or a phospholipase, such as phospholipase A2, for improved feed efficiency. See, e.g., WO 97/41739, U.S. Pat. No. 6,162,473, and U.S. Pat. No. 6,183,739.

Likewise described have been feed compositions comprised of an enzyme, such as PI-PLC, that cleaves a linkage, thereby to effect release of a cell-surface protein or carbohydrate, for the treatment or prevention of digestive tract infection. See, e.g., WO 01/41785. Walsh et al., *J. Anim. Sci.* 73: 1074 (1995), discuss feed compositions comprising glucanase enzymes that cleave a mixed link glucan substrate, such as 1,4-β-glucanase which cleaves mixed β-1,3, β-1,4-substrates. In our tests, however, neither PI-PLC nor 1,4-β-glucanase displayed immune-stress reducing activity.

There has been no description heretofore of a feed composition comprised of an enzyme that is other than a β-mannanase-type hemicellulase or a phospholipase and that is present in an amount effective to reduce immunological stress.

Accordingly, there is a need for compositions and methodology for reducing immunological stress in animals.

SUMMARY OF THE INVENTION

One embodiment provides a composition suitable for oral administration to an animal comprising an immune stress-reducing enzyme in an orally acceptable carrier. The composition is selected from the group consisting of: (i) an animal feed comprising an amount of the enzyme effective to decrease the level of positive acute phase protein in the animal, increase the level of negative acute phase protein in the animal, and/or improve animal growth performance; (ii) a liquid composition other than an animal feed comprising at least 40,000 IU enzyme/L; and (iii) a solid composition other than an animal feed comprising at least 40,000 IU enzyme/kg. The enzyme is other than a β-mannanase-type hemicellulase or phospholipase, and, if the enzyme comprises 1,3-β-glucanase, the composition is selected from the group consisting of (i) an animal feed comprising at least 20 IU 1,3-β-glucanase/kg feed; (ii) a liquid composition other than an animal feed comprising at least 155,000 IU 1,3-β-glucanase/L and (iii) a solid composition other than an animal feed comprising at least 300,000 IU 1,3-β-glucanase/kg.

In one embodiment, the composition is an animal feed comprising at least 20 IU enzyme/kg feed. In another embodiment, the composition is a solid composition other than an animal feed comprising at least 80,000 IU enzyme/kg, or at least 160,000 IU enzyme/kg.

In one embodiment, the composition is an animal feed that comprises an ingredient that induces an immune response in the animal and the enzyme comprises an enzyme that degrades said ingredient. In one embodiment, the ingredient is an antigen displayed by a pathogenic microorganism.

In one embodiment, the enzyme comprises 1,3-β-glucanase. In one embodiment, the enzyme comprises 1,3-β-glucanase and the composition is selected from the group consisting of (i) an animal feed comprising at least 30 IU 1,3-β-glucanase/kg feed; (ii) a liquid composition other than an animal feed comprising at least 230,000 IU 1,3-β-glucanase/L and (iii) a solid composition other than an animal feed comprising at least 450,000 IU 1,3-β-glucanase/kg.

Another embodiment provides a composition suitable for oral administration to an animal comprising two or more immune stress-reducing enzymes, wherein the composition comprises at least one immune stress-reducing enzyme other than 1,4-β-mannanase and 1,3-β-glucanase. The composition is selected from the group consisting of: (i) an animal feed comprising an amount of said immune stress-reducing enzymes effective to decrease the level of positive acute phase protein in said animal, increase the level of negative acute phase protein in said animal, and/or improve animal growth performance; (ii) a liquid composition other than an animal feed comprising at least one immune stress-reducing enzyme in an amount of at least 40,000 IU enzyme/L; and (iii) a solid composition other than an animal feed comprising at least one immune stress-reducing enzyme in an amount of at least 40,000 IU enzyme/kg.

In one embodiment, the composition is an animal feed comprising at least one immune stress-reducing enzyme in an amount of at least 20 IU enzyme/kg feed. In another embodiment, the composition is a solid composition other than an animal feed comprising at least one immune stress-reducing enzyme in an amount of at least 80,000 IU enzyme/kg, or at least 160,000 IU enzyme/kg.

In specific embodiments, the composition is selected from the group consisting of (i) a composition comprising 1,4-β-mannanase and chitanase; (ii) a composition comprising 1,4-β-mannanase and xyloglucanase; (iii) a composition comprising 1,4-β-mannanase and arabinanase; (iv) a composition comprising 1,3-β-glucanase and chitanase; (v) a composition comprising 1,3-β-glucanase and xyloglucanase; (vi) a composition comprising 1,3-β-glucanase and arabinanase and (vii) a composition comprising 1,4-β-mannanase, 1,3-β-glucanase and arabinanase.

Another embodiment provides a composition suitable for oral administration to an animal comprising 1,4-β-mannanase and 1,3-β-glucanase. The composition is selected from the group consisting of (i) an animal feed comprising 1,4-β-mannanase and at least 20 IU 1,3-β-glucanase/kg feed, (ii) a liquid composition other than an animal feed comprising 1,4-β-mannanase and at least 155,000 IU 1,3-β-glucanase/L and (iii) a solid composition other than an animal feed comprising 1,4-β-mannanase and at least 300,000 IU 1,3-β-glucanase/kg. In one embodiment, the composition is selected from the group consisting of (i) an animal feed comprising 1,4-β-mannanase and at least 30 IU 1,3-β-glucanase/kg feed; (ii) a liquid composition other than an animal feed comprising 1,4-β-mannanase and at least 230,000 IU 1,3-β-glucanase/L and (iii) a solid composition other than an animal feed comprising 1,4-β-mannanase and at least 450,000 IU 1,3-β-glucanase/kg. In one embodiment, the composition further comprises one or more additional immune stress-reducing enzymes.

Another embodiment provides a method of improving animal growth performance and/or reducing immune stress in an animal, comprising orally administering to the animal any of the compositions described above.

In one embodiment, the animal is administered an ingredient that induces an immune response in the animal and the composition comprises at least one immune stress-reducing enzyme that degrades the ingredient. In one embodiment, the ingredient and enzyme are administered in the same composition. In one embodiment, the composition is an animal feed. In one embodiment, the ingredient is an antigen displayed by a pathogenic microorganism.

Another embodiment provides a method of preventing or treating infection associated with a pathogenic microorganism that displays an antigen, comprising orally administering to an animal in need thereof any of the compositions described above, wherein the composition comprises at least one immune stress-reducing enzyme that degrades the antigen.

DETAILED DESCRIPTION

Figure 1:
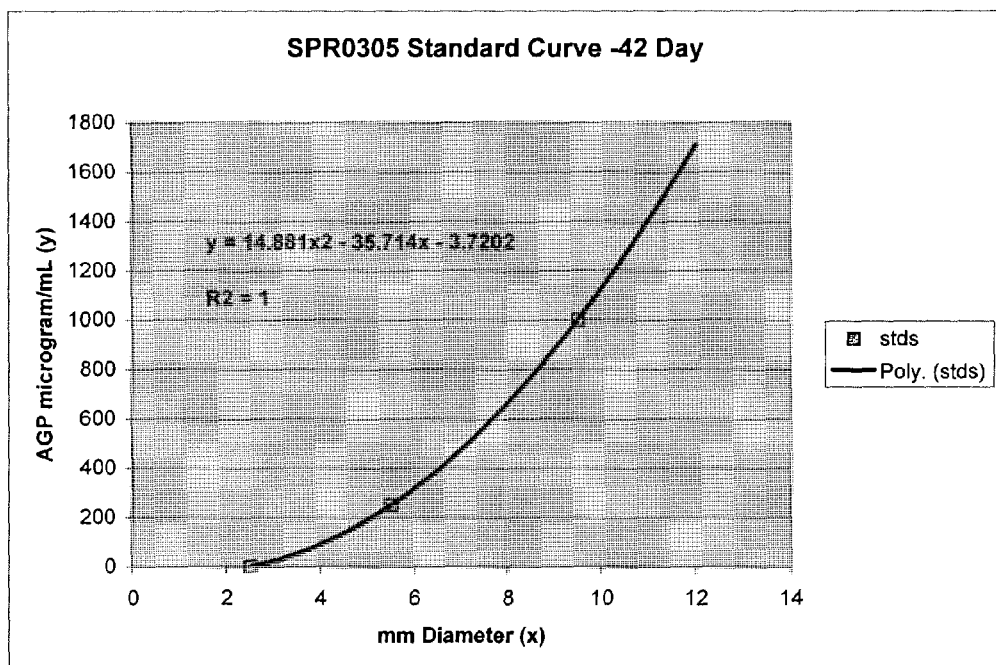
FIG. 1 shows the best curve fit (and underlying polynomial equation) for calculating the concentration of chicken α-1-acid glycoprotein (AGP) in plasma samples of test chickens with data obtained in Example 1.

As used in the following discussion, the terms "a" or "an" should be understood to encompass one or more, unless otherwise specified.

As used herein, the term "animal" refers to any animal, including humans and other animals, including companion animals such as dogs and cats, livestock, such as cows and other ruminants, buffalo, horses, pigs, sheep, fowl (e.g., chicken, ducks, turkeys, and geese) and aquaculture animals (e.g., fish and shrimp and eels).

In the present description, the phrases "enzyme that degrades an antigen" and "enzyme that degrades an ingredient" mean that the enzyme converts the antigen or ingredient to a form that is not recognized by the animal's immune system. The ability of an enzyme to degrade an antigen or ingredient can be identified by measuring the animal's serum APP concentration, whereby a decrease in the serum concentration of positive APP, or an increase in the serum concentration of negative APP, indicates that the enzyme has degraded the antigen or ingredient.

As noted above, the term "APP" include "negative" proteins whose concentration decreases with stress, and "positive" proteins whose concentration increases with stress. The invention includes compositions and methods that increase the concentration of negative acute phase proteins whose concentration typically decreases with stress, as well as compositions and methods that decrease the concentration of positive acute phase proteins whose concentrations typically increase with stress. For convenience, in the discussion that follows, the invention is exemplified with reference to the effect of the compositions and methods on positive acute phase proteins. Thus, the term "APP" in the discussion that follows generally refers to any one or more positive acute phase proteins associated with an animal's stress response. It should be understood that the compositions and methods described herein as decreasing the concentration of "APP" (referring to positive acute phase proteins) also are useful for increasing the concentration of negative acute phase proteins.

One aspect of the invention relates to a composition comprising an enzyme that is effective to reduce the immunological stress experienced by an animal. For convenience, these enzymes are referred to herein as "immune stress-reducing" enzymes. As used herein, the term "immune stress-reducing enzyme" means any enzyme that degrades an antigen or molecular pattern that is recognized by the animal's immune system, e.g., an antigen or molecular pattern that triggers an immune response, thereby causing the animal to experience immunological stress. The term "molecular pattern" as used herein includes general molecular patterns that are bound by receptors in the context of the innate immune system, such as molecular patterns that are usually associated with pathogens.

In accordance with one embodiment, the immune stress-reducing enzyme is not a β-mannanase-type hemicellulase. In one accordance with that embodiment, the immune stress-reducing enzyme is not endo-1,4-β-D-mannanase. In accordance with another embodiment, the enzyme is not a phospholipase. In accordance with another embodiment, the immune stress-reducing enzyme is not 1,4-β-D-glucanase. In accordance with another embodiment, the immune stress-reducing enzyme is not PI-PLC. In accordance with another embodiment, the immune stress-reducing enzyme is not a β-mannanase-type hemicellulase or a phospholipase. In accordance with yet another embodiment, the immune stress-reducing enzyme is not a β-mannanase-type hemicellulase, is not 1,4-β-glucanase, and is not a phospholipase. In accordance with a further embodiment, the immune stress-reducing enzyme is not a β-mannanase-type hemicellulase, is not 1,4-β-glucanase, is not a phospholipase, and is not PI-PLC.

While not wanting to be bound by any theory, the present inventors believe that the immune stress-reducing enzyme's degradation of the antigen or molecular pattern inhibits or reduces the immune response triggered by the antigen or molecular pattern, thereby reducing the animal's immunological stress. The reduction in immunological stress can be identified and monitored by measuring the animal's serum APP concentration, using methods known in the art for quantifying APP. Examples of such methods are referenced in Murata, et al., supra, and are described and referenced in Hulten et al., *Vet. Microbial.* 95: 75 (2003) and Holt et al., supra, as well as in Example 1 below.

In a related embodiment, the invention provides methods for reducing immunological stress in an animal that comprise administering to the animal a composition comprising an amount of an immune stress-reducing enzyme effective to reduce the level of APP in the animal.

A number of different positive acute phase proteins have been identified, including α-1-acid glycoprotein (AGP), ceruloplasmin (Cp), proteins of the collectin family (e.g., lung surfactant proteins, conglutinin and mannan-binding lectin), fibrinogen (Fb), C-reactive protein (CRP), haptoglobin, protease inhibitors (e.g., α-1-antitrypsin, α-1-antichymotrypsin, and α-2-macroglobulin) and serum amyloid-A (SAA). Other potential APP include lipopolysaccharide-binding protein (LPB), phospholipid-binding proteins such as annexins and Major Acute Phase Protein (MAP). Murata, et al., supra. Serum concentrations of any one of these or other APP can be used to identify, assess and monitor enzyme activity in accordance with the invention.

Different APP may play more significant roles in the stress responses of different animals. For example, AGP is known to be clinically important in cattle, and is associated with infection in pigs, dogs, cats and chicken (including hens). Cp has been reported to be an indicator of infection in cattle, horses, and chickens. CRP has been identified in ruminants, horses, pigs, dogs, and cats, although it has not been demonstrated that CRP is an APP in cattle. CRP has been shown to be associated with infection in horses and pigs. Fb is a reliable indicator of inflammation, bacterial infection or surgical trauma in cattle and sheep, and is associated with infection in horses. Hp is an APP in a number of production and companion animals, including ruminants such as cattle, sheep, pigs, horses, and dogs. SAA has been associated with inflammation and infection in cattle and with infection in horses, pigs, companion animals such as dogs, and chicken. An increase in SAA milk levels has been found in cows and ewes with mastitis. Serum LBP has been associated with infection in cattle, as has local levels of annexins (on the surfaces of secretory epithelia in lungs of infected cattle). MAP is reported to be an indicator of infection in pigs. Additionally, while transferrin is usually considered a negative acute phase protein, it appears to play a role as a positive acute phase protein in chickens. Murata, et al., supra; Holt et al., Poultry Sci. 81: 1295-1300 (2002). Others also have reported that SAA and Hp, as well as CRP and MAP, are associated with infection in pigs. Hulten et al., supra.

In some embodiments, the compositions of the invention comprise an amount of immune stress-reducing enzyme that is effective to decrease the serum concentration of APP in an animal. The amount may vary depending on the animal and the immune stress-reducing enzyme, and can readily be determined by those skilled in the art using methods known in the art. For example, an animal's serum APP levels can be measured prior and subsequent to administration of the enzyme, or serum APP levels of equivalent treated and control animals can be compared. (In this regard, it may be advantageous to compare treated and control animals of the same age, as APP levels may change with age. For example, we have found that serum AGP levels increase with chicken age.) A decrease in serum APP concentration associated with administration of the enzyme indicates that an effective amount of enzyme was administered.

In other embodiments, the compositions of the invention comprise an amount of immune stress-reducing enzyme that is effective to improve animal growth performance (also referred to as "live performance," particularly in the field of poultry). As used herein, the phrase "animal growth performance" includes any parameter that reflects animal growth, including feed conversion, water absorption, feces water content, uniformity of body weight within a flock or group of animals, livability, and mortality. While not wanting to be bound by any theory, it is believed that, under some conditions, the effect of the immune stress-reducing enzyme on APP concentration is masked by factors such as immune stress-inducing factors, such as the presence of a low-level infection in a group of animals or stressful living conditions. Under such conditions, the immune stress-reducing enzyme may nevertheless be effective to improve animal growth performance. Thus, animal growth performance is an alternative measure of the effectiveness of the compositions and methods of the present invention.

The composition may be any composition suitable for administration to an animal. In one embodiment, the composition is suitable for oral administration. In one specific embodiment, the composition that is suitable for oral administration is generally recognized as safe for oral administration to an animal. In another specific embodiment, the composition that is suitable for oral administration contains only ingredients, and amounts of said ingredients, that are generally recognized as safe for oral administration to an animal. In another specific embodiment, the composition that is suitable for oral administration does not contain any ingredients, or amounts of said ingredients, that are not generally recognized as safe for oral administration to an animal. In another specific embodiment, the composition that is suitable for oral administration contains only ingredients, and amounts of said ingredients, that are allowed, or that are not prohibited, for oral administration to an animal. In another specific embodiment, the composition that is suitable for oral administration does not contain any ingredients, or amounts of said ingredients, that are not allowed, or that are prohibited, for oral administration to an animal.

In some embodiments, the composition comprises an orally acceptable carrier for the enzyme. As used herein, "orally acceptable carrier" includes any physiologically acceptable carrier suitable for oral administration. Orally acceptable carriers include without limitation animal feed compositions, aqueous compositions, and liquid and solid compositions suitable for use in animal feed products and/or for oral administration to an animal. Suitable carriers are known in the art, and include those described in U.S. Pat. No. 6,780,628.

In some embodiments, the composition is an animal feed. As used herein, the term "animal feed" has its conventional meaning in the field of animal husbandry. For example, animal feed includes edible materials which are consumed by livestock for their nutritional value. Animal feed includes feed rations, e.g., compositions that meet an animal's nutritional requirements, and also include compositions that do not meet an animal's nutritional requirements.

In specific examples of such an embodiment, the amount of enzyme is at least about 50,000 international units (IU) per U.S. ton of feed, at least about 60,000 IU per ton of feed, at least about 70,000 IU per ton of feed, at least about 80,000 IU per ton of feed, at least about 90,000 IU per ton of feed, at least about 100,000 IU per ton of feed, at least about 200,000 IU per ton of feed, or at least about 500,000 IU per ton of feed, or higher.

In other specific examples, the invention provides an animal feed comprising an amount of immune stress-reducing enzyme of at least about 20 IU/kg feed, such as at least 20 IU/kg feed, at least at 25 IU/kg feed, at least at 30 IU/kg feed, at least at 35 IU/kg feed, at least at 40 IU/kg feed, at least at 45 IU/kg feed, at least 50 IU/kg feed, or more. While not wanting to be bound by any theory, it is believed that an animal feed comprising an amount of immune stress-reducing enzyme of at least about 20 IU/kg feed will be effective to decrease the level of positive acute phase protein in said animal, increase the level of negative acute phase protein in said animal, and/or improve animal growth performance.

Thus, in some embodiments, the invention provides an animal feed comprising an amount of immune stress-reducing enzyme effective to decrease the level of positive acute phase protein in the animal, increase the level of negative acute phase protein in the animal, and/or improve animal growth performance The feed composition may be prepared by methods known in the art. For example, immune stress-reducing enzyme can be added to the other feed ingredients at any stage during the manufacturing process, as deemed to be appropriate by those skilled in the art. In one embodiment, the enzyme is provided as a solution, such as a liquid enzyme concentrate that is added to other feed ingredients during the manufacturing process. Alternatively, an enzyme-containing solution is sprayed on to a substantially final form of the animal feed. In another embodiment, the enzyme is provided as a solid composition (such as a powder), such as a solid composition that is added to other feed ingredients during the manufacturing process. Exemplary methods for manufacturing enzyme-containing feed are described in WO 97/41739.

In some embodiments, the composition is other than an animal feed. For example, the composition may be a liquid composition other than an animal feed or a solid composition other than an animal feed. Such compositions may be suitable for direct administration to an animal or may be used as a feed additive (e.g., added to feed prior to feeding) or a feed supplement (including supplements that are diluted with other feed components prior to feeding and supplements that are offered to an animal on a free choice, separate basis). Examples of a liquid composition other than an animal feed include liquid enzyme concentrates, including liquid enzyme concentrates that are typically diluted or combined with other ingredients prior to oral administration to an animal.

In embodiments where the composition is a liquid composition other than an animal feed, such as an enzyme solution, the liquid composition or solution may comprise at least about 40,000 international units (IU) per liter of solution, such as at least 40,000 IU/L, at least 50,000 IU/L, at least 60,000 IU/L, at least 70,000 IU/L, at least 80,000 IU/L, at least 90,000 IU/L, at least 100,000 IU/L, at least about 500,000 IU/L, at least about 600,000 IU/L, at least about 700,000 IU/L, at least about 800,000 IU/L, at least about 900,000 IU/L, at least about 1,000,000 IU/L, at least about 2,000,000 IU/L, or at least about 5,000,000 IU/L.

In some embodiments, an amount of liquid composition other than an animal feed, such as about 500 mL solution, is applied to or combined with an amount of feed, such as to a ton of feed, to arrive at feed formulations with enzyme levels described above. In other embodiments, an amount of liquid composition other than an animal feed is applied to or combined with an amount of feed to prepare an animal feed with an amount of enzyme effective to decrease the level of positive acute phase protein in the animal, increase the level of negative acute phase protein in the animal, and/or improve animal growth performance.

It is believed that currently available liquid enzyme concentrate compositions (other than the 1,3-β-glucanase compositions discussed below) that are suitable for oral administration comprise much less than at least about 40,000 IU/L of an immune stress-reducing enzyme, if any at all, and are not effective to decrease the level of positive acute phase protein, increase the level of negative acute phase protein, and/or improve animal growth performance, when used in accordance with their instructions.

In embodiments where the composition is a solid composition other than an animal feed, the composition may comprise at least about 40,000 IU/kg, such as at least 40,000 IU/kg, at least 50,000 IU/kg, at least 60,000 IU/kg, at least 70,000 IU/kg, at least 80,000 IU/kg, at least 90,000 IU/kg, at least 100,000 IU/kg, at least 120,000 IU/kg, at least 140,000 IU/kg, at least 160,000 IU/kg, at least 180,000 IU/kg, at least 200,000 IU/kg, or more.

In some embodiments, an amount of a solid composition other than an animal feed is applied to or combined with an amount of feed to arrive at feed formulations with enzyme levels described above. In other embodiments, an amount of solid composition other than an animal feed is combined with an amount of feed to prepare an animal feed with an amount of enzyme effective to decrease the level of positive acute phase protein in the animal, increase the level of negative acute phase protein in the animal, and/or improve animal growth performance.

It is believed that currently available solid enzyme powder compositions that are suitable for oral administration comprise much less than at least about 40,000 IU/kg of an immune stress-reducing enzyme, if any at all, and are not effective to decrease the level of positive acute phase protein, increase the level of negative acute phase protein, and/or improve animal growth performance, when used in accordance with their instructions.

As conventional in the art, the term "IU" or "international unit" refers to an amount of enzyme that will catalyse the transformation of 1 micromole of the substrate per minute under conditions that are optimal for the enzyme. Weight equivalents to international units of immune stress-reducing enzymes are known in the art and can be determined using standard assays. Exemplary standard assays for representative immune stress-reducing enzymes are outlined below.

In one embodiment, the enzyme is expressed by a plant that is used in animal feed. For example, corn can be genetically engineered to express an immune stress-reducing enzyme and the resulting genetically modified corn product can be used in feed. Production also can be effected with other genetically modified or classically modified systems such as bacteria, e.g., *E. coli, Bacillus* sp., *Lactobacillus*; yeast, e.g., *Pichia, Yarrow, Saccharomyces, Schizosaccharomyces* (e.g., *Schizosaccharomyces pomb, Hansenula, Kluyveromyces, Candida*), and other fungus, such as *Aspergillus, Rhizopus, Tricoderma, Humicola, Penicillium,* and *Humicola*.

In accordance with another embodiment, the immune stress-reducing enzyme is provided in a capsule or tablet from for oral ingestion. The invention also encompasses embodiments where the enzyme is administered by other routes, such as intravenously, peritoneally, or subcutaneously, as a component of a composition formulated for such administration in accordance with known pharmacological practices.

An animal's immune system may recognize as an antigen or molecular pattern certain ingredients of a feed composition that do not pose a real threat to the animal's health. Nonetheless, the ingredient triggers an immune response that causes the animal to experience immunological stress, and that can be identified and monitored by an increase in the serum concentration of one or more APP. While not wanting to be bound by any theory, the present inventors believe that this "unnecessary and counterproductive" immune response may involve pattern recognition receptors (PRR), such as those involved in the innate immune system.

The innate immune system provides an immune response that does not depend on specific antigen recognition. See, e.g., Tosi, *J. Allergy Clin. Immunol.* 116: 241 (2005). One aspect of the innate immune system involves PRR, which recognize and bind pathogen-associated molecular patterns, transducing immune response signals. See, e.g., Fabrick et al., *J. Biol. Chem.* 279: 26605 (2004). Examples of PRR include Toll-like receptors (TLR) that recognize a range of molecular patterns and generate intracellular signals for activation of a range of host responses. See, e.g., Tosi, supra; Blach-Olszewska, *Arch. Immunol. Ther. Exp.* 53: 245 (2005). PRR/TLR have been identified that recognize mannose (e.g., Blach-Olszewska, supra), 1,3-β-glucan (e.g., Rice et al., *J. Leukoc. Biol.* 72:140 (2002)), lipopolysaccharide and phosphorylcholine (e.g., Baumgarth et al., *Semin. Immunopathol.* 26: 347 (2005)), lipoteichoic acid, phenol-soluble modulin, muramyl dipeptide and peptidoglycan (e.g., Fournier et al., *Clin. Microbiol. Rev.* 18: 521 (2005). Immunomodulatory receptors for mannan (e.g., Klabunde et al., *Parasitol. Res.* 88: 113 (2002) (mannan-binding lectin)), and N-acetyl-D-glucosamine and N-acetyl-D-mannosamine (e.g., Hansen et al., *J. Immunol.* 169: 5726 (2002)). TLRs for double stranded RNA (e.g., Bell et al., *Proc. Nat'l Acad. Sci. USA* 102: 10976 (2005)) and DNA with methylation patterns that differ from endogenous DNA (e.g., Huang at al., *J. Immunol.* 175: 3964 (2005); Normemacher et al., *Infect. Immun.* 71: 850 (2003)) also have been identified.

While these molecular patterns are associated with pathogenic microorganisms (e.g., bacteria, viruses, fungi and protozoa) they also are presented by some non-pathogenic molecules, such as animal feed ingredients. An innate immune response to non-pathogenic molecules presenting these molecular patterns unnecessarily subjects an animal to immunological stress, and may detrimentally impact the animal's feed efficiency, slow the animal's rate of weight gain or result in weight loss, make the animal more susceptible to infection, increase the animal's body temperature, or otherwise have a negative impact on the animal's health or food energy (calorie) utilization efficiency. The innate immune response resulting from MBL (mannose-binding lectin) function, for example, induces powerful responses. It has been shown that mutation of one of the mannose binding protein's genes in mice paradoxically allows survival from a normally lethal acute septic peritonitis challenge (Takahashi, K. et al., *Microbes Infect.* 4 (8): 773-784, 2002). The immune stress from aggressive innate immune response is more lethal than the infection in this case.

β-mannan is a component of soybean products and soybean-based animal feeds. High molecular weight forms of β-mannan present in animal feed can trigger an "unnecessary and counterproductive" innate immune response, thereby subjecting the animal to immunological stress. The present inventors found that this immunological stress can be reduced or prevented using a β-mannanase-type hemicellulase, endo-1,4-β-D-mannanase, an enzyme which degrades β-mannans (e.g. β-galactomannan, β-glucomannan), thereby reducing or preventing the immune response to β-mannan. As shown in the Examples below, the reduction in immunological stress is reflected in a decrease in serum APP concentration.

α-mannanase, which degrades α-mannan, is useful as an immune-stress reducing enzyme in accordance with the invention. α-mannan is not considered to be a hemicellulose because it does not share characteristic properties of hemicelluloses.

In the field of industrial enzymes, the term "hemicellulase" has been used as a trade name for β-mannanase. Likewise, patents and publications co-authored by the inventors use the term "hemicellulase" to refer to β-mannanase, including endo-1,4-β-D-mannanase. See, e.g., U.S. Pat. No. 6,162,473. In other contexts, the term "hemicellulase" may be broader, encompassing glucanases and xylanases in addition to mannanase, as explained below.

The term "hemicellulose" was coined to describe carbohydrate plant material obtained by extraction with a dilute alkaline solution that is hydrolyzed more easily than cellulose. See, e.g., Schulze, E., *Berichte der Deutschen Botanischen Gesellschaf,* 24: 2277 (1891); Schulze, E., *Z. Physiol. Chem.* 16: 387 (1892). Since then, "hemicellulose" has come to specify water insoluble plant polysaccharides associated with cellulose, other than pectin and starches and polysaccharides in plant sap, that are soluble in dilute alkali solutions. See, e.g., Whisler et al., "Hemicelluloses," in IV POLYSACCHARIDE CHEMISTRY 112 (Academic Press, 1953). Xylan, β-mannans and galactans are generally considered to be hemicelluloses, although some β-mannans, like Locust bean gum and guar gum galactomannans are readily soluble. Softwood trees have a lot of β-mannans associated with their cellulose and hardwoods have a lot of xylans.

In contrast to hemicelluloses, α-mannan is associated with fungal cells walls, such as *Saccharomyces*, is not a structural component of wood, and is uniformly found in eucaryotic glycoproteins that are generally soluble in water. Thus, α-mannan is not considered to be a hemicellulose, and α-mannanase is not a hemicellulase. α-mannanase is useful as an immune stress-reducing enzyme in accordance with the present invention because it degrades α-mannans that are recognized by an animal's immune system, but that are not pathogen associated. The innate immune system is sensitive to mannan because polymers containing mannose are found on the surface of many pathogens.

Other feed ingredients that may be recognized by an animal's immune system include β-1,3-glucan (a common structural component of plant materials), N-linked glycoprotein complexes (found, for example, in soybean products), double-stranded RNA from plants, animals or microbes, and DNA from microbes, plants or animals with a foreign (non-endogenous) methylation pattern. Thus, in accordance with one embodiment, the invention provides a composition comprising one or more immune stress-reducing enzymes that degrade one or more of these or other feed ingredients. In a related embodiment, the invention provides methods for reducing immunological stress in an animal that comprise administering to the animal a composition comprising an effective amount of such an enzyme or enzymes. Specific examples of immune stress-reducing enzymes and the antigens they degrade are set forth in the following table. The invention encompasses compositions that comprise other immune stress-reducing enzymes that degrade the same or different antigens, as well as the use of such other enzymes to reduce immunological stress.

| ANTIGENS | ENZYMES |
|---|---|
| α-mannan | α-mannanase |
| | α-mannosidase |
| β-mannans | β-mannanase |
| | hemicellulase (β-mannanase type) |
| | 1,4-β-mannanase |
| | endo-1,4-β-D-mannanase |
| β-1,3-glucans | 1,3-β-glucanase |
| | Endo-1,3-β-glucanase |
| | (EC 3.2.1.39) |
| | β-glucosidase |
| double stranded RNA | non-specific nuclease |
| non-capped mRNA | RNAse L |
| 3pRNA | dsRNA specific adenosine deaminase |
| DNA | DNAase |
| | non-specific nuclease |
| | CG specific restriction endonuclease |
| N-linked glycoproteins | carbohydrases |
| (e.g., asialoglycoprotein) | N-glycanases |
| | endo enzymes |
| | PNGases |
| phosphocholine in sphingomyelin | sphingomyelinase |
| N-acetylglucosamine containing | chitinase |
| polymer, (e.g., chitin) | (EC 9 3.2.1.14) |
| | chitin deacetylase |
| | carbohydrate deacetylase |
| | N-acetylglucosaminidase |
| phosphatidylserine | phosphatidylserine decarboxylase |
| | phospholipase C |
| | phospholipase D |
| sulfated galactoside-saccharide | sulfatase |
| β-galactoside | β-galactosidase |
| xyloglucan | xyloglucanase |
| | (EC 3.2.1.15) |

| ANTIGENS | ENZYMES |
|---|---|
| lipoarabinomannan (LAM) arabinogalactan (AG) | arabinanase |
| hyaluronan (hyaluronic acid) | hyaluronidase (EC 3.2.1.35) |
| arabinogalactan and other arabino-modifided carbohydrates | α-arabinofuranosidase |
| chondroitin sulfate | chondroitinase |
| glucocerebrosides | glucocerebrosidase |
| methyl esters of carbohydrates | methyl esterase |
| ferulic acid esterified carbohydrates | ferulic acid esterase furuloyl esterase |
| acetylated carbohydrate polymer | acetyl esterase carbohydrate deacetylase |

In accordance with some embodiments, the invention provides a composition comprising two or more immune stress-reducing enzymes. In one embodiment, at least one of the two or more enzymes is not 1,4-β-mannanase or 1,3-β-glucanase. In another embodiment, a composition comprises 1,4-β-mannanase and 1,3-β-glucanase.

In one specific embodiment, the composition is an animal feed comprising 1,4-β-mannanase and at least about 20 IU 1,3-β-glucanase/kg feed, such as at least 20 IU/kg feed, at least 25 IU/kg feed, at least 30 IU/kg feed, at least 35 IU/kg feed, at least 40 IU/kg feed, at least 45 IU/kg feed, at least 50 IU/kg feed, or more, of 1,3-β-glucanase.

In another specific embodiment, the composition is a liquid composition other than an animal feed comprising 1,4-β-mannanase and at least about 155,000 IU 1,3-β-glucanase/L, such as at least 155,000 IU/L, at least 230,000 IU/L, at least 300,000 IU/L, at least 380,000 IU/L, or more, of 1,3-β-glucanase.

In another specific embodiment, the composition is a solid composition other than an animal feed comprising 1,4-β-mannanase and at least about 300,000 IU 1,3-β-glucanase/kg, such as at least 300,000 IU/kg, at least 450,000 IU/kg, at least 600,000 IU/kg, at least 750,000 IU/kg, at least 900,000 IU/kg, or more, of 1,3-β-glucanase.

In another embodiment, a composition comprises 1,4-β-mannanase and xyloglucanase. In another embodiment, a composition comprises 1,3-β-glucanase and xyloglucanase. In another embodiment, a composition comprises 1,4-β-mannanase and chitinase. In another embodiment, a composition comprises 1,3-β-glucanase and chitinase. In another embodiment, a composition comprises 1,4-β-mannanase and arabinanase. In another embodiment, a composition comprises 1,3-β-glucanase and arabinanase. In another embodiment, a composition comprises 1,4-β-mannanase, 1,3-β-glucanase and arabinanase.

It will be understood that these combinations are exemplary only, and the invention includes compositions comprising other combinations of immune stress-reducing enzymes. For example, the invention includes compositions comprising any one or more of the immune stress-reducing enzymes listed above and/or discussed below and 1,4-β-mannanase.

Immune stress caused by a feed ingredient may not always be an innate immune system response. It is well known that a certain small percentage of infants fed soy protein-based human milk-replacer formula develop a strong detrimental immunological-based intestinal reaction (see the report from the Committee on nutrition, American Academy of Pediatrics, *Pediatrics* 101 (1): p 148, (1998)). N-linked Gycoproteins in soy, for example β-conglycinin, some times referred to as 7S globulin (Ogawa T, et al., *Biosci. Biotechnol. Biochem.* 59(5):831-833, 1995; Burks A W, et al., *J Pediatr.*

Gastroenterol. Nutr. 8(2):195-203, 1989) can be strong antigens and are recognized as having anti-nutritional qualities. β-conglycinin is deliberately removed from soy protein isolate preparations used for nutritional supplements despite its contribution to total protein. Hydrolysis destroys the antigenicity. In addition, we have found that an enriched 7S soy glycoprotein fraction used in feeding roosters was less well digested than another less glycosylated soy protein fraction.

Examples of suitable enzymes for degrading carbohydrates in N-linked glycoproteins include α-fucosidases such as α-1,2-fucosidase and α-1,3-1,4-fucosidase, α-mannosidases such as α-1,6-mannosidase, α-1,2-mannosidase, and α-1,3-mannosidase, β-1,4-galactosidase, endo-β-N-acetylglucosaminidase F (endo F), peptide-N—(N-acetyl-beta-glucosaminyl)asparagine amidase F (PNGase F), PNGase A, endo-β-N-acetylglucosaminidase H (endoH), endo D, endo C, α-N-acetylgalactosaminidase, β-1,3-galactosidase, endo-N-acyl-neuraminidase (endo N), α-2,3-neuraminidase, α-2,6-neuraminidase, α-2,8-neuraminidase, β-N-acetylhexosaminidase, endo-β-N-galactosidase, endo-α-N-acetylglactosaminidase, endo-α-1,6-D-mannanase, arabinogalactanase, α-galactosidase, β-galactosidase.

These enzymes are known in the art and some are available from commercial sources. Alternatively, immune stress-reducing enzymes can be obtained from microorganisms that produce enzymes, such as bacteria, fungi and yeast. Additionally, the enzymes can be obtained using recombinant technology methods known in the art, by, for example, genetically engineering a host cell to produce an enzyme, e.g., causing transcription and translations of a gene encoding the enzyme. The amino acid sequences of a number of the enzymes set forth above are known in the art. Using those sequences or known nucleotide sequences encoding those sequences, those skilled in the art can design suitable genes for recombinant expression of the enzymes. Additionally or alternatively, a nucleotide sequence encoding a known immune stress-reducing enzyme can be used to probe a DNA library to identify other nucleotide sequences encoding immune stress-reducing enzymes. As known in the art, such a DNA library can be derived from a defined organism or population of organisms, or can be obtained from natural sources and thus represent DNA from microorganisms that are difficult to culture.

In embodiments where the composition comprises a combination of enzymes, the enzyme may be produced individually, by separate organisms, or two or more of the enzymes may be produced by a single organism. For example, a single organism can be recombinantly engineered to produce two or more enzymes by methods known in the art.

As discussed above, an animal's immune system recognizes a number of different molecular patterns displayed by pathogenic microorganisms, including lipopolysaccharide (associated with, for example, gram negative bacteria), bacterial flagella containing the conserved protein flagellin, peptidoglycan (associated with, for example, gram positive bacteria), lipotechoic acid (associated with, for example, gram positive bacteria) is bound by the C-type lectin L-Ficolin, (Lynch, N. J., et al., *J. Immunology* 172: 1198-1202, 2004), phosphorylcholine (associated with, for example, gram positive and gram negative bacteria), DNA (such as bacterial DNA with CpG non-methylated motifs, see Van Uden and Raz, *J Allergy Clin Immunol.* 104(5):902-10, 1999.), and double-stranded RNA and 3pRNA (Hornung, et. al., *Science* 314: 994-997, 2006). The immune response to these molecules includes an increase in serum APP.

Other pathogenic molecular patterns include N-acetylglucosamine containing molecules and N-acetylmannosamine containing molecules. The exact binding specificity of all collectins (mannose-binding lectin is a collectin or C-type lectin) may not be known, but binding to a number of different bacterial pathogens is observed by for example, H-ficolin, surfactant-associated protein A (SP-A), and conglutinin. Compounds like N-acetylglucosamine and N-acetylmannosamine can inhibit the binding and thus are presumed to be part of the pattern recognition binding specificity (Haurum, J. S., et al., *Biochemical J.* 293 (3): 873-878, 1993).

Examples of other antigens and molecular patterns that can be targeted for enzyme degradation in accordance with the invention include bacterial lipoproteins (Hacker, H. et al., *J. Exper. Med.* 192 (4): 595-600, 2000); R-1,3-glucan binding by the collectin Dectin-1 (Adachi, Y., et al., *Infection and Immunity* 72 (7): 4159-4171, 2004); flagellin (which bind the TLF5) (Honko, A. N., and Mizel, S. B., *Immunol. Res.* 33 (1): 83-101, 2005); fucosyl glycoconjugates; α-Gal-ceramide; fibrinogen; heparin sulfate; sulfated gal-saccharide; chitosan, N-acetylglucosamine; asialoglycoprotein; and β-galactosides.

The class of receptors called scavenger receptors (SR) are structurally related to some of the innate immune response receptors, and may create immune stress. It is believed that SR are involved in the recycle and clean up of apoptosis or otherwise damaged cells. The scavenger receptors (SR) expressed by macrophages and dendritic cells are also receptors for the innate immune system. Moreover, some SR recognize pathogens and some innate immune receptors are shown to be important for apoptosis. Thus, in accordance with one embodiment of the invention, the molecular pattern binding targets of SR are targeted for enzyme degradation.

One such SR molecular pattern-binding target is oxidized low density lipoprotein (LDL). The receptors called LOX-1 (Peiser, L., et al., *Current Opinion in Immunology* 14:123-128, 2002) SR-PSOX/CXCL-16 (Fukumoto, N., et al., *J. Immunol.* 173(3): 1620-1627, 2004) and CD36 (Bruni, F., et al., *Clin. Appl. Thromb. Hemost.* 119(4): 417-28, 2005) bind oxidized-LDL that may be present in some feeds, particularly feeds containing animal by-product meals such as blood meals.

Another SR molecular pattern binding target is phosphatidlyserine (PS) and lyso phosphatidlyserine (lyso PS). SR for PS include SR-PSOX/CXCL-16 and other PS receptors (Schlegel, R. A. and Williamson, P., *Cell Death Differ.* 8 (6): 545-548, 2001). Exposure to phosphatidylserine phospholipids may lead to inflammatory responses and phosphatidylserine phospholipids are believed to present in most feeds at some level.

Hyaluronan is abundant in extracellular fluids in animals, but is also recognized by innate immune/scavenger system mechanisms, for example, in wound healing. See, e.g., Jameson, et al., *J. Expt. Medicine* 210 (8): 1269-1279, 2005. Chicken combs are a commercial source of hyaluronan, typically used in the purified form of hyaluronic acid. Thus, poultry meal made from byproducts of meat processing can contain hyaluronan, often in abundant amounts. Hyaluronidase (EC 3.2.1.35), which degrades hyaluronan and hyaluronic acid, is useful as an immune-stress reducing enzyme in accordance with the invention, particularly in the context of animals that are fed poultry meal. For example, hyaluronidase is useful in reducing immune stress associated with feeding poultry meal.

Enzymes that degrade any of these molecular patterns thereby inhibit or reduce the immune response, thus reducing the animal's immunological stress. For example, DNAases and non-specific nucleases are known that degrade double-stranded RNA and bacterial DNA. Restriction endonuclease enzymes specific for methylated CG motifs in non-mamalian DNA are known. Enzymes that degrade phosphorylcholine include phosphorylcholine hydrolyase, alkaline phosphatase, acid phosphatase, phosphorylcholine esterase, and phosphorylcholine phosphatase.

This stress reduction can be identified and monitored by measuring the level of serum APP, as described above, with decreased serum APP concentrations reflecting reduced immunological stress.

As noted above, the composition comprises an amount of immune stress-reducing enzyme that is effective to decrease the level of acute phase protein in the animal. This amount may vary from animal to animal, and from enzyme to enzyme, but readily can be determined by those skilled in the art, for example, by measuring APP levels, as described above. For example, an animal's serum APP levels can be measured prior and subsequent to administration of the enzyme, or serum APP levels of treated and control animals can be compared. In embodiments where the effective amount is assessed by measuring serum APP levels prior and subsequent to administration of the enzyme, the subsequent measurement can be made from at least about one day to at least about several days or longer after initial administration of the enzyme. A decrease in serum APP concentration associated with administration of the enzyme indicates that an effective amount of enzyme was administered. It should be understood, however, that APP levels generally decrease as the animal's adaptive immune response takes effect.

In accordance with some embodiments, the present invention provides composition comprising 1,3-β-glucanase in an amount effective to effective to decrease the level of positive acute phase protein in said animal, increase the level of negative acute phase protein in said animal, and/or improve animal growth performance. In one specific embodiment, the composition is an animal feed comprising at least about 20 IU 1,3-β-glucanase/kg feed, such as at least 20 IU/kg feed, at least 25 IU/kg feed, at least 30 IU/kg feed, at least 35 IU/kg feed, at least 40 IU/kg feed, at least 45 IU/kg feed, at least 50 IU/kg feed, or more, of 1,3-β-glucanase. In another specific embodiment, the composition is a liquid composition other than an animal feed comprising at least about 155,000 IU 1,3-β-glucanase/L, such as at least 155,000 IU/L, at least 230,000 IU/L, at least 300,000 IU/L, at least 380,000 IU/L, or more, of 1,3-β-glucanase. In another specific embodiment, the composition is a solid composition other than an animal feed comprising at least about 300,000 IU glucanase/kg, such as at least 300,000 IU/kg, at least 450,000 IU/kg, at least 600,000 IU/kg, at least 750,000 IU/kg, at least 900,000 IU/kg, or more, of 1,3-β-glucanase.

In some animal feed embodiments where the enzyme comprises 1,3-β-glucanase, the enzyme may be present in amount that is at least about 100,000 IU per ton feed.

Figure 3:
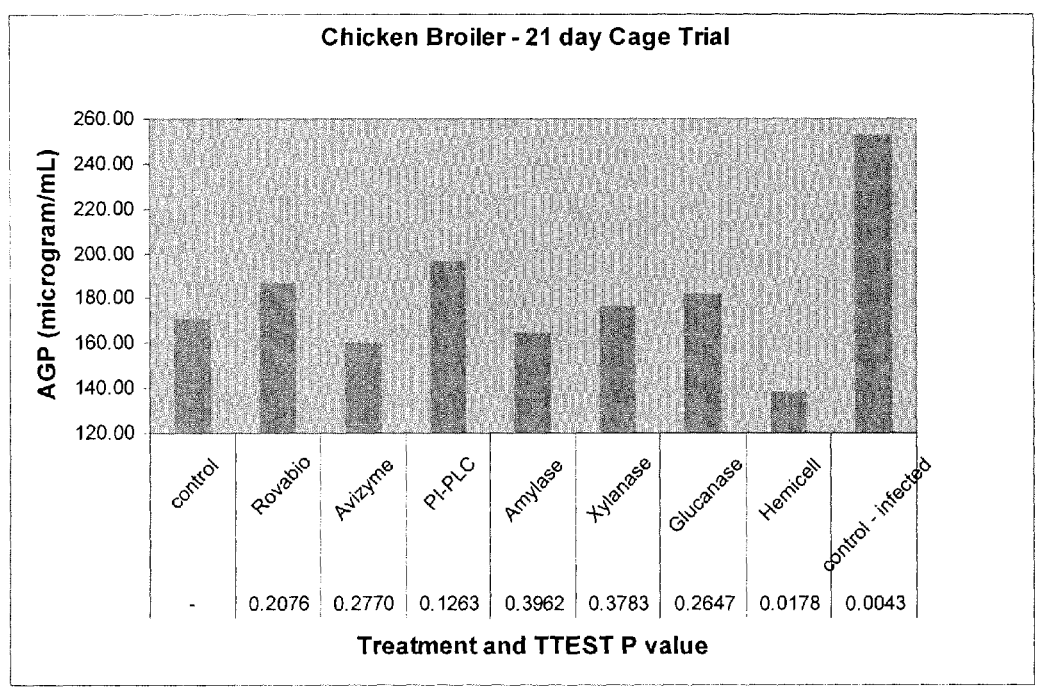
FIG. 3 shows the AGP levels of serum from chickens receiving one of several different feeds, including feeds in accordance with the invention and prior art feeds, as described in Example 3.

These amounts are much higher than the 1,343-glucanase content of commercial feed enzyme additives and commercially available feeds, which the present inventors have analyzed and found to provide at most from about 10,000 IU/ton feed, about 72,500 IU/L non-feed liquid composition, or about 150,000 IU/kg non-feed solid composition. The present inventors do not believe that 10,000 IU/ton feed 1,3-β-glucanase would be effective to reduce APP, and confirmed this belief experimentally. The present inventors also determined experimentally that commercial products such as Avizyme® (Danisco A/S, Langebrogade 1, Dk-1001, Copenhagen, Denmark) and Rovobio (Adisseo France SAS, 42, Avenue Aristide Briand, BP100, 92164 Antony Cedex,) and commercial feeds comprising standard amounts of β-1,3-1,4-glucanase (Brewzyme™ BG plus, Dyadic International, 140 Intracoastal Pointe Drive, Suite 404, Jupiter, Fla. 33477-5094), xylanase (Multifect® XL, Genencor International, Inc., 925 Page Mill Road, Palo Alto, Calif.), PI-PLC (ChemGen Corp., 211 Perry Parkway, Gaithersburg, Md.) and amylase (Amylase FRED, Genencor International, Inc., 925 Page Mill Road, Palo Alto, Calif.) do not reduce APP. See Example 3 below and FIG. 3. In the cases where 1,3-β-glucanase activity is present, it is within the low ranges noted above and not effective to reduce AGP.

In another embodiment, the immune stress-reducing enzyme is provided as a component of a composition that also comprises the antigen or molecular pattern containing compounds that are degraded by the enzyme. For example, the invention includes an animal feed comprising β-1,3-glucan and a 1,3-β-glucanase; an animal feed comprising DNA or double-stranded RNA and a DNAase or and non-specific nucleases; an animal feed comprising an N-linked glycoprotein and an endo- or exo-carbohydrase, N-glycanase, or PNGase, or any of the other enzymes set forth above. Other suitable combinations of antigens and immune stress-reducing enzymes will be apparent to those skilled in the art, and are encompassed by the invention.

In this embodiment, it is expected that serum APP levels will remain elevated as long as the composition is administered. Thus, if the effective amount of immune stress-reducing enzyme is assessed by measuring serum APP levels prior and subsequent to administration of the enzyme, the subsequent measurement can be made days or weeks after initial administration of the enzyme.

As noted above, the invention includes methods of reducing immune stress in an animal, comprising administering to the animal a composition comprising an immune stress-reducing enzyme in an amount effective to decrease the level of acute phase protein in the animal. The composition may be any composition described above, including an oral composition, such as animal feed, a liquid composition other than an animal feed, or a solid composition other than an animal feed. The animal may be any animal, including a human, and may be a healthy animal or an animal suffering from infection or other disease or condition.

The invention also includes methods of improving animal growth performance, comprising administering to the animal a composition comprising an immune stress-reducing enzyme. In some embodiments, the composition comprises an amount of immune stress-reducing enzyme effective to improve animal growth performance. The composition may be any composition described above, including an oral composition, an animal feed, a liquid composition other than an animal feed, or a solid composition other than an animal feed. The animal may be any animal, including a human, and may be a healthy animal or an animal suffering from infection or other disease or condition.

In one embodiment, the enzyme is expressed by a plant that is used in animal feed. For example, corn can be genetically engineered to express an immune stress-reducing enzyme and the resulting genetically modified corn product can be used in feed.

In one embodiment, the animal is administered the immune stress-reducing enzyme and also is administered the antigen (e.g., the pattern-containing molecule degraded by the enzyme). The enzyme and antigen may be administered separately or simultaneously as part of the same or different compositions. In one embodiment, the animal is administered a feed comprising the antigen or pattern containing molecule, and is separately administered a composition comprising the immune stress-reducing enzyme. In another embodiment, the animal is administered a feed comprising the antigen or pattern containing molecule and a feed supplement comprising the enzyme. In another embodiment, the animal is administered a feed comprising both the antigen and the enzyme.

Another aspect of the invention provides compositions and methods for reducing immunological stress by preventing and treating infection caused by pathogenic microorganisms. Sometimes animals consume compositions, such as water or animal feed, that comprise pathogenic microorganisms (e.g., bacteria, viruses, fungi and protozoa), or are otherwise exposed to such pathogens. The present invention provides compositions comprising an enzyme that degrades pathogenic microorganism's key components (i.e., a "pathogenic component"), in an amount effective to decrease infection and therefore the level of APP expressed in the animal responding to the infection. The composition is useful for reducing immunological stress through preventing or minimizing the infection thereby decreasing the immunological stress caused directly by the pathogen. In one particular aspect of this embodiment, the invention provides a method preventing and treating digestive tract infection.

By degrading pathogen components, enzymes may also treat or prevent infection. That is, because a pathogenic component is degraded, the pathogen could lose its ability to infect the host. This decrease in actual infection would result in reduced immune stress and reduction in serum APP by a different mechanism than described above, but in practice indistinguishable in terms of the observed APP reduction. There are at least three scenarios where enzymatic treatment could have a positive result. If the pathogen molecular structure degraded by the enzyme is involved in binding of the pathogen to the host cells, the first step required for infection, or any other key step necessary for successful infection, then enzymatic treatment could help. Alternatively, the binding structure on the host cell might be modified. For example a number of bacterial and protozoan pathogens have been shown in interact with proteoglycans on the eukaryotic host cells surface, particularly sulfated proteoglycans (Flekenstein, J. M. et al., *Infection and Immunity* 70 (3): 1530-1537, 2002). The application of enzymes such as heparinase, and N-acetylglucosamine-4-sulfatase, or arylsulfatases could reduce the interaction and infection.

In a second scenario the pathogen molecular structure degraded could be a toxin that disrupts the target cell's metabolic functions. In a third scenario, the pathogenic component degraded by the enzyme might be involved in the pathogen's mechanism to evade the host immune response. Numerous immune response evasion mechanisms have evolved in pathogens ranging from mimicking the host ells outer appearance to inhibiting immune response, for example complement reactions or apoptosis. The reduction or prevention of infection also can be assessed by measuring serum APP, with higher APP levels being associated with infection.

Enzymes that degrade pathogenic components, such as those described above, are known in the art. For example, an endosialidase derived from a bacteriophage was shown to prevent the lethality of *E. coli* K1 systemic infection of rats by degrading the PSA (polysialic acid) capsule on the bacteria surface. Although degrading the capsular carbohydrate has no effect on the viability of the *E. coli* in vitro, loss of capsule in vivo allows recognition and control of the infection by the host immune system eliminating lethality (Mushtaq, N., et al. *Antimicrobial Agents and ChemoTherapy* 48(5):1503-1508, 2004). The PSA capsule allows the *E. coli* surface to look like a host cell thus evading host innate immune responses. Another known enzyme useful in the present invention is heparinase I (Neutralase™, Ibex Technologies, Canada). Many enzymes are available from commercial sources or can be obtained from microorganisms that produce enzymes, such as bacteria, and fungi including yeast, or can be produced recombinantly, as discussed above.

Desired enzymes can be produced by recombinant DNA techniques when the gene coding for the enzyme is known. The advancement of rapid DNA sequencing methodology has resulted in large public databases of proteins and their gene coding sequences, such as the NCBI Genbank. Using rapid sequencing technology from, for example, 454 Life Sciences (454 Life Sciences, 20 Commercial Street, Branford, Conn. 06405), a typical bacterial genome can be sequenced in four hours. A previously unknown gene of new desired enzyme from the genome can be obtained by probing the genome using, for example, previously identified coding sequences from the same type or similar types of enzymes described in commercial or public databases, using readily available computer programs such as Blast. Those skilled in the art can identify DNA in the genome that has a threshold level of homology to the known sequence and other properties of a gene-coding region, and then isolate and amplify the gene using, for example, polymerase chain reaction (PCR) technology. The gene can then be expressed in a host and its desired protein enzymatic properties can be confirmed.

If a desired enzyme activity is not previously known, then it can be located using standard microbiology enrichment techniques selecting for growth on the substrate. Microbes using the substrate as the sole carbon or nitrogen source must express enzymes capable of degrading the target compound. In order to develop economical production, one has the choice to improve the production of that enzyme using classical mutation/selection or enrichment methods with the producing microorganism, or through recombinant DNA expression methods well known in the art.

The composition comprising an immune stress-reducing enzyme that degrades a pathogenic microorganism may be any composition suitable for administration to an animal, including compositions suitable for oral administration to an animal, as described above. As noted above, the composition may comprise an amount of enzyme that is effective to decrease the level of positive acute phase protein (or increase the level of negative acute phase protein) in the animal and/or improve animal growth performance. This amount may vary from animal to animal, and from enzyme to enzyme, but readily can be determined by those skilled in the art, for example, by measuring APP levels and/or monitoring animal growth performance, as described above and as known in the art.

In one embodiment, the immune stress-reducing enzyme that targets a pathogenic antigen is provided as a component of an animal feed. In one example of this embodiment, the amount of enzyme is at least about 100,000 IU/ton feed.

In another embodiment, the immune stress-reducing enzyme that targets a pathogenic antigen is provided as a component of a composition that also comprises the pathogenic antigen. For example, the invention includes an animal feed comprising (A) a pathogenic microorganism displaying an antigen such as lipopolysaccharide, peptidoglycan, lipotechoic acid, phosphorylcholine, double-stranded RNA and DNA and (B) and enzyme that degrades the antigen. Pathogenic organisms can find the way into feed due to the inherent nature of unsanitary conditions caused by the dense growth of animals in production situations.

As noted above, the invention includes methods of reducing immune stress in an animal and/or of improving animal growth performance, comprising administering to the animal a composition comprising an immune stress-reducing enzyme. In one embodiment, the animal is administered the immune stress-reducing enzyme that degrades a pathogenic antigen and also is administered the pathogenic antigen. The enzyme and antigen may be administered separately or simultaneously as part of the same or different compositions. In one embodiment, the animal is administered a feed comprising the antigen, and is separately administered a composition comprising the enzyme. In another embodiment, the animal is administered a feed comprising the antigen and a feed supplement comprising the enzyme. In another embodiment, the animal is administered a feed comprising both the antigen and the enzyme.

The following examples further illustrate the invention, but the invention is not limited to the specifically exemplified embodiments.

EXAMPLE 1

An animal feed comprising hemicellulase (endo-1,4-β-mannanase) was prepared and administered to chickens and AGP levels were measured, as described in more detail below.

A total of 4000 one-day-old male Cobb×Cobb chicks were allocated at random to 8 experimental treatments, and each treatment was replicated 10 times:

| Experimental Design: | |
|---|---|
| Total No. of pens: | 8 Treatments |
| Total No. of Treatments: | 80 |
| No. of birds per pen: | 8 |
| No. of pens per Treatment: | 50 |
| No. of birds per Treatment: | 10 |
| | 500 |

Two of the eight treatments comprised stress-reducing enzymes in accordance with the invention: Treatment 3 (mannanase in the form of evaporated whole cell broth of *B. lentus* fermentation applied at approximately 100 MU/ton in the basal diets) and Treatment 6 (mannanase in the form of cell-free centrifuged supernatant of *B. lentus* fermentation broth applied at approximately 30 MU/ton in the basal diets). Treatment 8 was a control with no added enzyme. (1 MU=4000 IU)

The basal meal feed batches were divided evenly in eight parts and each was sprayed with the appropriate amount of the test materials. Starter and Grower feeds contained 90 g/ton Cobon™ (an anticoccidial drug of the ionophore type) plus 50 g/ton BMD® (antibiotic). Finisher feeds were non-medicated.

Starter Diets were offered to all birds from day-old until 21 days of age, Grower Diets from 22-35 days, and Finisher Diets from 36-42 days. The diets and water were provided ad libitum. The diets were presented to the birds as crumbles/pellets during all feeding periods. Tap water was used as drinking water and supplied by an internal water system network.

Composition and Analyses of the Basal Experimental Diets

| Ingredients | Starter | Grower | Finisher |
|---|---|---|---|
| Corn | 60.3851 | 67.6864 | 72.1098 |
| Soybean meal (48.5% CP) | 34.5066 | 27.8363 | 23.3785 |
| Fat AV Blend | 1.0516 | 0.9915 | 1.1389 |
| Dicalcium phosphate | 1.761 | 1.2682 | 1.3021 |
| Limestone flour | 1.3192 | 1.383 | 1.26 |
| Sodium chloride | 0.3299 | 0.3304 | 0.3305 |
| DL Methionine | 0.2135 | 0.0793 | 0.0552 |
| L-lys.hcl | 0.008 | — | — |
| Choline chloride 70% | 0.05 | 0.05 | 0.05 |
| Vitamin premix | 0.25 | 0.25 | 0.25 |
| Mineral premix | 0.075 | 0.075 | 0.075 |
| Coban, g/ton | 90 | 90 | — |
| BMD, g/ton | 50 | 50 | — |
| Calculated Analyses[2] | | | |
| ME$_n$ poultry (kcals/kg) | 3080.0 | 3150.0 | 3200.0 |
| Dry matter, % | 88.9169 | 88.9236 | 88.9054 |
| Crude protein, % | 22.0 | 19.3 | 17.5 |
| Crude fibre, % | 2.8813 | 2.8176 | 2.7632 |
| Fat, %, | 3.6777 | 3.8291 | 4.0981 |
| Calcium, % | 1.0 | 0.9 | 0.85 |
| Total phosphorus, % | 0.7088 | 0.5967 | 0.5877 |
| Available phosphorus, % | 0.45 | 0.35 | 0.35 |
| Sodium, % | 0.18 | 0.18 | 0.18 |
| Lysine, % | 1.2 | 1.0152 | 0.8948 |
| Methionine + Cysteine, % | 0.92 | 0.72 | 0.65 |
| Threonine, % | 0.8821 | 0.7657 | 0.6932 |
| Tryptophan, % | 0.2938 | 0.2489 | 0.2185 |

Two birds from each of the ten pens in Treatments 3, 6 and 8 were randomly selected for blood analysis at the end of the 42 days after weighing, for a total of 20 birds out of the 500 per treatment. Samples were collected onto ice in blood collection tubes containing anti-coagulant heparin, and plasma was obtained by centrifugation.

Blood plasma samples were assayed for chicken α-1-acid glycoprotein using an immunodiffusion based assay kit from Cardiotech Services, Inc. (Louisville, Ky.). Serum samples taken from the two birds/pen were added to the test plates (5 μL per well) and to some wells standard pure AGP was added at concentrations ranging up to 1000 μg/mL. Precipitin rings were measured using a precipitin ring measurement scale to the nearest 0.1 mm diameter.

A polynomial equation was used to provide the best curve fit with the data and to allow the rapid calculation of the concentration of AGP in the plasma samples as shown in FIG. 1.

The measurements of precipitin ring diameters for all the recovered chicken serum samples and the calculated AGP concentration for each bird is shown in the table below. The birds fed mannanase on average have a very statistically significant decrease in the average AGP concentration compared to the control birds.

42 Day Blood Samples (y=AGP ug/ML; x=ring measurement in mm)

| Treatment 3 (Mannanase) | | Treatment 8 (control) | | Treatment 6 (Mannanase) | |
|---|---|---|---|---|---|
| X | y | x | y | X | y |
| 5.3 | 225.0 | 6 | 317.7 | 5.3 | 225.0 |
| 5.3 | 225.0 | 6 | 317.7 | 5.7 | 276.2 |
| 4.9 | 178.6 | 6.1 | 332.1 | 5.8 | 289.7 |
| 5.2 | 212.9 | 5.2 | 212.9 | 5.1 | 201.2 |
| 5.8 | 289.7 | 7.4 | 546.9 | 5.4 | 237.4 |
| 5.4 | 237.4 | 5.4 | 237.4 | 5.7 | 276.2 |
| 5.4 | 237.4 | 6.2 | 346.9 | 5.5 | 250.0 |
| 5.9 | 303.6 | 5.9 | 303.6 | 6.1 | 332.1 |
| 5.6 | 262.9 | 6 | 317.7 | 5.4 | 237.4 |
| 5.9 | 303.6 | 6.2 | 346.9 | 5.2 | 212.9 |
| 5.2 | 212.9 | 6.1 | 332.1 | 5 | 189.7 |
| 5.4 | 237.4 | 5.6 | 262.9 | 6.1 | 332.1 |
| 5.3 | 225.0 | 5.9 | 303.6 | 5.5 | 250.0 |
| 5.1 | 201.2 | 6.3 | 361.9 | 5.5 | 250.0 |
| 5.3 | 225.0 | 6.2 | 346.9 | 6 | 317.7 |
| 5.3 | 225.0 | 7.5 | 565.5 | 5.4 | 237.4 |
| 5.7 | 276.2 | 7.4 | 546.9 | 5.6 | 262.9 |
| 5.3 | 225.0 | 7.5 | 565.5 | 4.4 | 127.2 |
| 5.7 | 276.2 | 7.5 | 565.5 | | |

-continued

| Treatment 3 (Mannanase) | | Treatment 8 (control) | | Treatment 6 (Mannanase) | |
|---|---|---|---|---|---|
| X | y | x | y | X | y |
| 5 | 189.7 | 6.1 | 332.1 | | |
| AVE | 238.5 | | 373.1 | | 250.3 |
| SD | 35.8 | | 115.6 | | 51.3 |
| CV | 14.99 | | 30.97 | | 20.50 |
| T Test p vs. 8 2.94E−05 | | | | T Test vs. 8 0.000193 | |

EXAMPLE 2

Another experiment using hemicellulase (endo-1,4-β-mannanase) was conducted. In this experiment, groups of chickens (10 pens each, with 50 birds per pen) were fed one of four diets:

Treatment 1 (control): Feed comprising BMD antibiotic sprayed post-pelleting with a control formulation, and 35% sorbitol with brown food dye, applied at 100 ml/ton feed.

Treatment 2 (control): Feed without BMD sprayed post-pelleting with a control formulation comprising 35% sorbitol with brown food dye, applied at 100 ml/ton feed.

Treatment 3: Feed sprayed post-pelleting with a formulation comprising hemicellulase (endo-1,4-β-mannanase) derived from *B. lentus*, applied at 100 ml/ton feed.

Treatment 4: Feed formulated with a powder composition (added into the mixer prior to pelleting) comprising hemicellulase (endo-1,4-β-mannanase) derived from *B. lentus* at 454 g of composition added/ton feed to provide 100 MU/tom of feed. (1 MU=4000 IU)

The chickens were 1 day old at the start of the experiment.

The diets were provided ad libitum. Starter (days 0-21), grower (days 21-35) and finisher (days 35-42) feeds with the following compositions were used as the base feeds:

Expected Amounts

| Nutrient Analysis | Starter | Grower | Finisher |
|---|---|---|---|
| ME POUL KCAL | 2960.0 | 3020.0 | 3080.0 |
| Crude Protein | 22.0 | 19.4 | 17.5 |
| Fat % | 3.1439 | 3.0647 | 3.4503 |
| Calcium % | 0.9 | 0.8 | 0.8 |
| T phos | 0.7032 | 0.6315 | 0.515 |
| A Phos | 0.45 | 0.39 | 0.35 |
| Sodium | 0.18 | 0.18 | 0.18 |
| Lysine % | 1.205 | 1.0302 | 0.9014 |
| Methionine | 0.5446 | 0.3838 | 0.3435 |
| Met + Cys | 0.92 | 0.72 | 0.65 |

Added Ingredients

| Ingredient | Starter | Grower | Finisher |
|---|---|---|---|
| Limestone | 0.8291 | 0.7674 | 0.9012 |
| Salt | 0.2696 | 0.2698 | 0.2702 |
| D-L Meth | 0.1963 | 0.0682 | 0.0532 |
| Choline Chloride 70% | 0.0500 | 0.0500 | 0.0500 |
| Dical P | 1.6869 | 1.4088 | 1.2295 |
| Fat | 0.6517 | 0.4751 | 0.8162 |
| Corn | 59.3480 | 67.4725 | 70.9038 |
| Soybean meal | 33.5934 | 27.1132 | 22.4010 |
| Poultry By-Product meal | 3.0 | 3.0 | 3.0 |
| Vitamin | 0.25 | 0.25 | 0.25 |
| Mineral | 0.075 | 0.075 | 0.075 |
| Salinomycin | 0.05 | 0.05 | 0.05 |

On day 21 approximately 3 ml of blood were collected from 3 birds per pen (30 per group). Blood was placed into a heparinized tube and lightly mixed. Tubes were slowly centrifuged and then serum was removed. Serum samples were placed into tubes with caps and labeled with pen number. Serum was frozen for subsequent AGP analysis, as described in Example 1 above. The immunodiffusion rings used to quantitate chicken α1 acid glycoprotein are easily measured, highly reproducible and exhibit a coefficient of variation of 4% or less.

Figure 2:
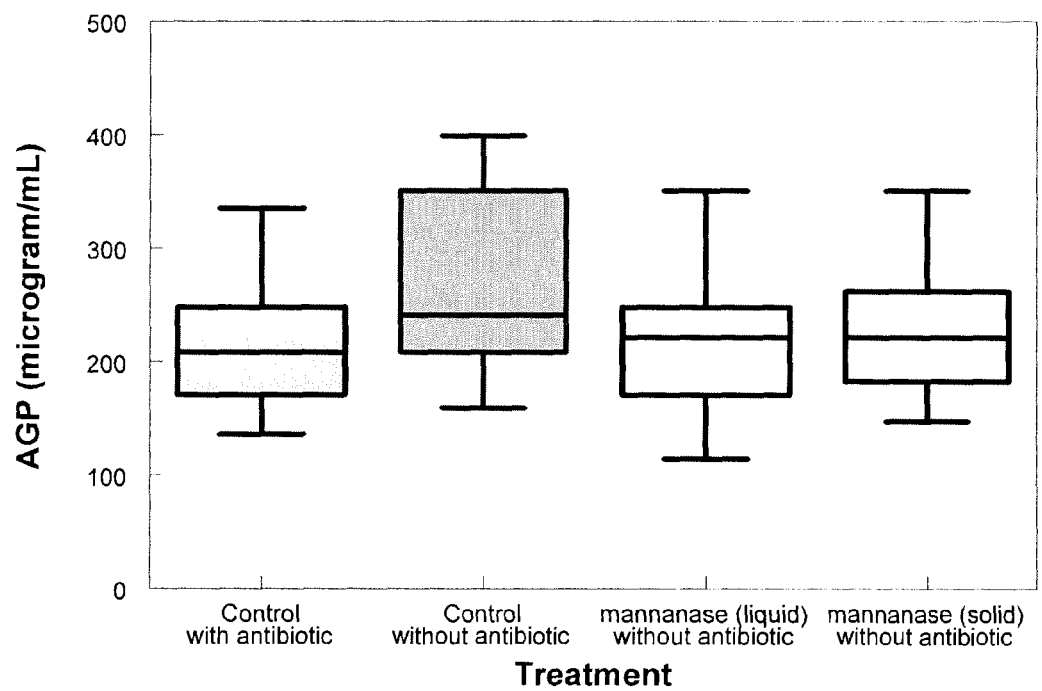
FIG. 2 is a Box and Wisker plot graphically showing the AGP levels in chicken serum from test chickens, as described in Example 2. The range of the data is represented by the vertical lines. The box represents the range of the data within one standard deviation of the mean. The horizontal line indicates the data mean.

The 21 day average results of 30 birds per treatment are shown in the table below and graphically in FIG. 2. It can be seen that leaving the antibiotic (BMD) out of the diet creates a large and significant increase in the plasma AGP level (compare Treatment 1 and Treatment 2). The addition of either hemicellulase (endo-1,4-β-mannanase) formulation into the no-BMD diet (Treatments 3 and 4) restored the AGP to the level seen with antibiotic use, indicating a significant reduction of immunological stress.

| | | Treatment | | | |
|---|---|---|---|---|---|
| | | 1 | 2 | 3 | 4 |
| AGP | Avg. | 214.35 | 267.99 | 220.28 | 233.09 |
| | SD | 62.16 | 82.42 | 68.58 | 67.73 |
| | CV | 29.00 | 30.76 | 31.13 | 29.06 |
| TTest | P vs. | | 0.003055 Trt. 1 | 0.008952 Trt. 2 | 0.03919 Trt. 2 |
| TTest | P vs. | | | | 0.234892 Trt. 3 |
| TTest | P vs. | | | 0.363305 Trt. 1 | 0.134383 Trt. 1 |

The growth performance of the chickens also was assessed, with the results summarized in the table below.

Growth Performance

| | FCR[1] | P val. | Wt. gain | P val. | Wt. adj. FCR[2] | P val. | CV of ID[3] | P val. |
|---|---|---|---|---|---|---|---|---|
| Day 21 | | | | | | | | |
| T1 | 1.394 | 0.150 | 0.693 | 0.016 | 1.379 | 0.017 | 13.81 | 0.33 |
| T2 | 1.412 | | 0.657 | | 1.424 | | 14.77 | |
| T3 | 1.404 | 0.605 | 0.673 | 0.197 | 1.404 | 0.248 | 14.03 | 0.46 |
| T4 | 1.407 | 0.740 | 0.670 | 0.459 | 1.410 | 0.551 | 14.40 | 0.69 |
| Day 42 | | | | | | | | |
| T1 | 1.776 | 0.006 | 2.102 | 0.189 | 1.772 | 0.007 | 11.23 | 0.19 |
| T2 | 1.813 | | 2.073 | | 1.820 | | 10.42 | |
| T3 | 1.770 | 0.001 | 2.131 | 0.088 | 1.756 | 0.005 | 9.97 | 0.49 |
| T4 | 1.761 | 0.0001 | 2.060 | 0.572 | 1.772 | 0.003 | 10.38 | 0.95 |

[1]FCR = Feed conversion
[2]Wt. Adj. FCR = weight adjusted feed conversion
[3]CV of ID = coefficient of variation in individual weights Thus, both feed conversion and weight adjusted feed conversion were improved at 21 days with statistical significance in chickens receiving β-mannanase. This indicates that the reduction in serum AGP can translate into real significance for animal performance.

EXAMPLE 3

The ability of other enzymes commonly used in animal feed were assessed for their possible effect on AGP. Commercial type chicken starter rations (low metabolic energy) were compounded with feedstuffs commonly used in the United States. These rations (in mash or crumble form) were fed ad libitum from the date of chick arrival until Day 21 of the study. Experimental treatment feeds were prepared from this basal starter feed. Treatment feeds were mixed to assure a uniform distribution of respective test article.

Composition and Analyses of the Basal Experimental Diets

| Ingredients | |
|---|---|
| Corn | 59.398 |
| Soybean meal (48.5% CP) | 33.5934 |
| Fat AV Blend | 0.6517 |
| Dicalcium phosphate | 1.6869 |
| Limestone flour | 0.8291 |
| Sodium chloride | 0.2696 |
| DL Methionine | 0.1963 |
| Poultry By Product Meal | 3.0 |
| Choline chloride 70% | 0.05 |
| Vitamin premix | 0.25 |
| Mineral premix | 0.075 |

| Ingredients | LO ME |
|---|---|
| $ME_n$ poultry (kcals/kg) | 2960 |
| Crude protein, % | 22.0 |
| Crude fibre, % | 2.8899 |
| Fat, %, | 3.1439 |
| Calcium, % | 0.9 |
| Total phosphorus, % | 0.7032 |
| Available phosphorus, % | 0.45 |
| Sodium, % | 0.18 |
| Lysine, % | 1.205 |
| Methionine + Cysteine, % | 0.92 |
| Threonine, % | 0.8266 |

BMD 50 g/t and Salinomycin 60 g/t were added to all feeds.

Enzyme Preparations

| Sample | enzyme | assay data | Stock vol | Diluent | Notes | Use Level |
|---|---|---|---|---|---|---|
| 3 | — | n.d. | | 20 | plus food coloring | 20 mL/100 Kg |
| 6 | Adessio, Rovabio Excel LC | Rovabio commercial product | 10 | 10 | | 20 mL/100kg |
| 7 | Danisco, Avizyme (1500 Granular) | Avizyme commercial product | Solid product | — | | 100 g/100 Kg |
| 8 | PI-PLC | 106 U/mL | 50 | — | | 1.0 mL/Kg |
| 9 | Genencor Amylase FRED | | | | | 20 mL/100 Kg |
| 10 | Genencor Multifect XL | | | | | 20 mL/100 Kg |
| 11 | Dyadic Brewzyme BG | | | | | 20 mL/100 Kg |
| 12 | Hemicell | 1092 MU/L | 13 | 12 | | 20 mL/100 Kg |
| 17 | — | n.d. | | 20 | plus food coloring | 20 mL/100 Kg |

(1 MU = 4000 IU)

Enzyme Preparations Further Information

| Sample | Main Activity | Use Level | Endo-1,3 β-glucanase minor activity* |
|---|---|---|---|
| 3 | — | | |
| 6 | Endo-1,4-β-Xylanase 350 AXC U/Ml Endo β-1,4-β-glucanase 500 AGL U/mL | Endo-1,4-β-Xylanase 350 AXC 63,350 AXC U/ton Endo β-1,4-β-glucanase 90,500 AGL U/ton | 9139 IU/ton |
| 7 | Amylase xylanase protease | 1.0 kg per ton | — |
| 8 | PI-PLC 106,000 IU/L | 96,188 IU/ton or 24 MU/ton | — |
| 9 | Amylase 4700 MU/L | $1.88 \times 10^6$ IU/ton or 470 MU/ton | — |
| 10 | Endo-1,4-β-Xylanase 4500 MU/L | 900,000 IU/ton or 225 MU/ton | — |
| 11 | Endo β-1,4-1,3-glucanase 1586 MU/L | 634,400 IU/ton or 159 MU/ton | 1040 IU/ton |
| 12 | Endo-1,4 β-mannanase 1092 MU/L | 400,000 IU/ton or 100 MU/ton | 580 IU/ton |
| 17 | — | | |

ChemGen MU = 4000 IU;
AXC - xylanase units defined by Adisseo;
AGL - glucanase units defined by Adisseo;
*approximate level measured by ChemGen Corp. by reducing sugar assay Feed and water were available ad libitum throughout the trial. On Day 15, birds in treatment 17 were orally inoculated with a mixed inoculum containing approximately 30,000 oocysts E. acervulina per bird, 2,500 oocysts of E. maxima per bird, and 25,000 oocysts E. tenella per bird. Coccidial oocyst inoculation procedures are described in SPR SOP: IN1.002.

Means for cage weight gain, feed consumption, and feed conversion are determined. The results are set forth below. Only animals receiving sample 17 were infected.

| Sample | Vs. Treatment 3 TTEST P= | Treatment | AGP ave | 21 Day Growth Data Avg. Live Wt. Gain | Conv. | Enzyme level per metric Ton |
|---|---|---|---|---|---|---|
| 3 | — | control | 170.52 | 0.624 | 1.438 | none |
| 6 | 0.2076 | Rovabio | 186.55 | 0.626 | 1.395 | 100 mL |
| 7 | 0.2770 | Avizyme | 160.44 | 0.633 | 1.426 | 1.0 kg |
| 8 | 0.1263 | PI-PLC | 196.35 | 0.650 | 1.406 | 106,000 IU |
| 9 | 0.3962 | Amylase | 164.05 | 0.622 | 1.434 | |
| 10 | 0.3783 | Xylanase | 175.89 | 0.593 | 1.444 | |
| 11 | 0.2647 | Glucanase | 182.00 | 0.629 | 1.396 | |
| 12 | 0.0178 | Hemicell | 138.22 | 0.645 | 1.421 | 102 MU |
| 17 | 0.0043 | control - infected | 252.04 | 0.564 | 1.507 | none |

We found that commercial feeds comprising standard amounts of amylase, 1,3-glucanase, 1,4-glucanase, xylanase and PI-PLC did not reduce AGP levels. Indeed, only hemicellulase (endo-1,4-β-mannanase) showed a significant effect on AGP levels. Additionally, comparing treatment 1 and 17 clearly shows that AGP is a highly responsive APP in chickens because infection increased the AGP level 82 μg/mL. See also FIG. 3.

EXAMPLE 4

Test animal feed comprising 1,3-β-glucan is formulated to include 1,3-β-glucanase at a concentration of 400,000 IU (100 ChemGen MU) per ton feed. The test animal feed is administered to test chickens, while control chickens receive the same animal feed (comprising 1,3-β-glucan) without 1,3-β-glucanase. After 21 and 42 days on this regimen, blood serum AGP levels are assessed as described above. Chickens receiving the enzyme-formulated animal feed have significantly lower levels of AGP than control animals. The test chickens also exhibit greater feed efficiency and improved weight gain as compared to control chickens.

EXAMPLE 5

Test animal feed comprising a source of bacterial DNA (e.g. Biolys® Lysine or other fermentation product containing cell products) is formulated to include non-specific nuclease derived from the Cyanobacterium *Anabaena* sp. 7120 (NucA), one of the most active non-specific nucleases known (Meiss, G. et al., *Eur. J. Biochem.* 251(3): 924-934, 1998). The enzyme is added at a concentration of $1\times10^7$ Kunitz Units enzyme/kg feed or approximately 1 mg (pure basis) per kg of feed. The test animal feed is administered to test chickens, while control chickens receive the same animal feed (comprising bacterial DNA) without non-specific nuclease. After 21 days or 42 days on this regimen, blood serum AGP levels are assessed as described above. Chickens receiving the enzyme-formulated animal feed have significantly lower levels of AGP than control animals.

EXAMPLE 6

Test animal feed comprising meat and bone meal, blood meal or other animal derived by-product is formulated to include phosphatidylserine decarboxylase at a concentration of 400,000 IU/ton of feed. The test animal feed is administered to test chickens, while control chickens receive the same animal feed without phosphatidylserine decarboxylase. After 21 days or 42 days on this regimen, blood serum AGP levels are assessed as described above. Chickens receiving the enzyme-formulated animal feed have significantly lower levels of AGP than control animals.

EXAMPLE 7

Test animal feed soy meal or other plant derived meal is formulated to include an α-mannanase and/or 1,3-β-glucanase enzymes derived from *B. lentus*, each at a concentration of 400,000 IU/ton of feed. The test animal feed is administered to test chickens, while control chickens receive the same animal feed without α-mannanase or 1,3-β-glucanase. After 21 days or 42 days on this regimen, blood serum AGP levels are assessed as described above. Chickens receiving the enzyme-formulated animal feed have significantly lower levels of AGP than control animals.

EXAMPLE 8

In this example Hemicell® mannanase added to feed (a conventional corn-soybean diet) was shown to reduce α1 acid glycoprotein (AGP) in turkey serum while also improving live growth performance. The experiment consisted of 48 pens of 11 tom turkeys (initial placement). The six treatments were replicated in 8 blocks, randomized within blocks of six pens each:

| | |
|---|---|
| No. Birds/Treatment | 88 |
| No. Reps/Treatment | 8 |
| Total Treatments | 6 |
| Total No. Pens | 48 |
| Total No. Birds | 528 |

One treatment that comprised stress-reducing enzymes in accordance with the invention, Treatment 1 (commercial Hemicell® with 100 MU/ton of feed) was analyzed for AGP. (1 MU=4000 IU) Treatment 2 was a control feed without added enzyme.

Feed was mixed to assure uniform distribution of basal feeds among treatments. All enzymes were mixed (sprayed on) to assure a uniform distribution of test enzymes and to assure similar feed condition between treatments. Each time treatment feed was made, a sample from the beginning, middle, and end of each treatment feed were mixed to form a composite sample. One sample was taken from the composite for each treatment, and for enzyme level verification.

The turkey diets fed in this study to Treatments 1 and 2 are described in detail below in the following tables. Tables show the composition of components, the calculated nutrient levels and finally some measured nutrient values with the returned feeds. The diets are representative of what might be used in a commercial turkey growing operation and thus the diet is adjusted several times throughout the 20-week period. Diet compositions were changed at 6, 9, 12, 15 and 18 weeks.

The diet compositions at each period are slightly different for Treatments 1 and 2. It is well known that Hemicell® mannanase has the effect of increasing the effective energy content of feeds (see U.S. Pat. No. 6,162,473). For that reason, the diets of Treatment 1 are formulated with fewer calories than the diets of Treatment 2 in order to minimize growth difference between Treatments 1 and 2 for the purpose of this study.

Ingredient Composition and Calculated Nutrient Levels, 0-9 Weeks

| | Period: | | | |
|---|---|---|---|---|
| | 0-6 weeks | | 6-9 weeks | |
| Ingredient (%) | Treatment 1 with Hemicell® | Treatment 2 | Treatment 1 with Hemicell® | Treatment 2 |
| Corn | 46.77 | 45.39 | 53.14 | 51.79 |
| Soybean meal | 37.15 | 37.40 | 29.30 | 29.50 |
| Poultry meal | 9.00 | 9.00 | 9.00 | 9.00 |
| Poultry Fat | 1.50 | 2.65 | 3.50 | 4.65 |
| Limestone | 1.20 | 1.20 | 1.25 | 1.25 |
| Dical phosphate 18.5 | 2.70 | 2.70 | 2.35 | 2.35 |
| Salt | 0.325 | 0.325 | 0.315 | 0.32 |
| DL Methionine | 0.315 | 0.315 | 0.245 | 0.25 |
| L-Lysine-HCl | 0.41 | 0.405 | 0.335 | 0.34 |
| Vitamin pre-mix | 0.25 | 0.25 | 0.25 | 0.25 |
| Trace minerals | 0.075 | 0.075 | 0.075 | 0.075 |
| Choline Cl 60% | 0.135 | 0.135 | 0.085 | 0.085 |
| Copper sulfate | 0.05 | 0.05 | 0.05 | 0.05 |
| Coban 60 g/lb | 0.055 | 0.055 | 0.05 | 0.05 |
| BMD 50 g/lb | 0.05 | 0.05 | 0.05 | 0.05 |
| Hemicell® | 0.0125 | 0.0 | 0.0125 | 0.0 |
| Crude protein (%) | 28.00 | 28.00 | 24.5 | 24.5 |
| ME (Kcal/lb) | 1323 | 1323 | 1408 | 1407 |
| Calcium (%) | 1.484 | 1.484 | 1.462 | 1.462 |
| A. Phosphorus (%) | 0.797 | 0.797 | 0.764 | 0.763 |
| Lysine (%) | 1.794 | 1.793 | 1.502 | 1.501 |
| Met + Cys (%) | 1.179 | 1.177 | 1.018 | 1.021 |

Ingredient Composition and Calculated Nutrient Levels, 9-15 Weeks

| | Period: | | | |
|---|---|---|---|---|
| | 9-12 weeks | | 12-15 weeks | |
| Ingredient (%) | Treatment 1 with Hemicell® | Treatment 2 | Treatment 1 with Hemicell® | Treatment 2 |
| Corn | 56.88 | 55.55 | 62.45 | 61.05 |
| Soybean meal | 24.55 | 24.75 | 21.15 | 21.40 |
| Poultry meal | 9.00 | 9.00 | 7.00 | 7.00 |
| Poultry Fat | 5.00 | 6.22 | 5.00 | 6.15 |
| Limestone | 1.20 | 1.20 | 1.15 | 1.15 |
| Dical phosphate 18.5 | 1.95 | 1.95 | 1.75 | 1.75 |
| Salt | 0.32 | 0.32 | 0.32 | 0.32 |
| DL Methionine | 0.22 | 0.22 | 0.30 | 0.30 |
| L-Lysine-HCl | 0.315 | 0.315 | 0.42 | 0.42 |
| Vitamin pre-mix | 0.25 | 0.25 | 0.25 | 0.25 |
| Trace minerals | 0.075 | 0.075 | 0.075 | 0.075 |
| Choline Cl 60% | 0.085 | 0.085 | 0.015 | 0.015 |
| Copper sulfate | 0.05 | 0.05 | 0.05 | 0.05 |
| Coban 60 g/lb | 0.05 | 0.05 | 0.00 | 0.00 |
| BMD 50 g/lb | 0.05 | 0.05 | 0.05 | 0.05 |
| Hemicell | 0.0125 | 0.0 | 0.0125 | 0.0 |
| Crude protein (%) | 22.5 | 22.5 | 20.0 | 20.0 |
| ME (Kcal/lb) | 1469 | 1469 | 1490 | 1490 |
| Calcium (%) | 1.35 | 1.35 | 1.19 | 1.19 |
| A. Phosphorus (%) | 0.681 | 0.681 | 0.59 | 0.59 |
| Lysine (%) | 1.350 | 1.350 | 1.298 | 1.298 |
| Met + Cys (%) | 0.940 | 0.940 | 0.95 | 0.95 |

Ingredient Composition and Calculated Nutrient Levels, 15-20 Weeks

| | Period: | | | |
|---|---|---|---|---|
| | 15-18 weeks | | 18-20 weeks | |
| Ingredient (%) | Treatment 1 with Hemicell® | Treatment 2 | Treatment 1 with Hemicell® | Treatment 2 |
| Corn | 67.25 | 65.85 | 70.60 | 69.15 |
| Soybean meal | 17.90 | 18.15 | 15.60 | 15.85 |
| Poultry meal | 5.00 | 5.00 | 4.00 | 4.00 |
| Poultry Fat | 6.00 | 7.15 | 6.50 | 7.70 |
| Limestone | 1.00 | 1.00 | 0.85 | 0.85 |
| Dical phosphate 18.5 | 1.50 | 1.50 | 1.23 | 1.23 |
| Salt | 0.33 | 0.33 | 0.34 | 0.34 |
| DL Methionine | 0.205 | 0.205 | 0.193 | 0.193 |
| L-Lysine-HCl | 0.340 | 0.340 | 0.235 | 0.235 |
| Vitamin pmx | 0.25 | 0.25 | 0.25 | 0.25 |
| Trace minerals | 0.075 | 0.075 | 0.075 | 0.075 |
| Choline Cl 60% | 0.02 | 0.02 | 0.02 | 0.02 |
| Copper sulfate | 0.05 | 0.05 | 0.05 | 0.05 |
| Coban 60 g/lb | 0.00 | 0.00 | 0.00 | 0.00 |
| BMD 50 g/lb | 0.05 | 0.05 | 0.05 | 0.05 |
| Hemicell | 0.0125 | 0.0 | 0.0125 | 0.0 |
| Crude protein (%) | 17.5 | 17.5 | 16.0 | 16.0 |
| ME (Kcal/lb) | 1539 | 1539 | 1570 | 1570 |
| Calcium (%) | 0.982 | 0.982 | 0.82 | 0.82 |
| A. Phosphorus (%) | 0.490 | 0.490 | 0.41 | 0.41 |
| Lysine (%) | 1.10 | 1.10 | 0.93 | 0.93 |
| Met + Cys (%) | 0.791 | 0.791 | 0.74 | 0.74 |

Diet Analysis with Returned Feeds, 0-12 Weeks

| | Treatment 1 with Hemicell® | | Treatment 2 | |
|---|---|---|---|---|
| Nutrient | Calculated | Analyzed | Calculated | Analyzed |
| | 0-3 weeks | | | |
| Protein | 28 | 27.46 | 28 | 27.57 |
| Fat | 4.2 | 4.03 | 5.3 | 4.99 |
| Calcium | 1.48 | 1.38 | 1.48 | 1.45 |
| T. Phosphorus | 1.02 | 0.96 | 1.02 | 1.08 |
| Hemicell units | 100 | 70.1 | 0 | 8.9 |
| | 3-6 weeks | | | |
| Protein | 28 | 25.90 | 28 | 27.17 |
| Fat | 4.2 | 4.01 | 5.3 | 5.16 |
| Calcium | 1.48 | 1.63 | 1.48 | 1.52 |
| T. Phosphorus | 1.02 | 1.15 | 1.02 | 1.12 |
| Hemicell units | 100 | 99.3 | 0 | 8.9 |

-continued

| Nutrient | Treatment 1 with Hemicell ® | | Treatment 2 | |
|---|---|---|---|---|
| | Calculated | Analyzed | Calculated | Analyzed |
| | 6-9 weeks | | | |
| Protein | 24.5 | 23.42 | 24.5 | 24.17 |
| Fat | 6.3 | 6.33 | 7.4 | 7.00 |
| Calcium | 1.46 | 1.69 | 1.46 | 1.65 |
| T. Phosphorus | 0.96 | 1.09 | 0.96 | 1.06 |
| Hemicell units | 100 | 138.6 | 0 | 14.4 |
| | 9-12 weeks | | | |
| Protein | 22.5 | 22.61 | 22.5 | 23.61 |
| Fat | 7.9/8.0 | 7.91 | 9.0 | 9.02 |
| Calcium | 1.35 | 1.37 | 1.35 | 1.32 |
| T. Phosphorus | 0.86 | 0.93 | 0.86 | 0.90 |
| Hemicell units | 100 | 83.9 | 0 | 12.0 |

Diet Analysis with Returned Feeds, 12-20 Weeks

| Nutrient | Treatment 1 with Hemicell ® | | Treatment 2 | |
|---|---|---|---|---|
| | Calculated | Analyzed | Calculated | Analyzed |
| | 12-15 weeks | | | |
| Protein | 20 | 20.49 | 20 | 21.09 |
| Fat | 7.79 | 8.25 | 8.89 | 9.03 |
| Calcium | 1.19 | 1.16 | 1.19 | 1.09 |
| T. Phosphorus | 0.76 | 0.78 | 0.76 | 0.77 |
| Hemicell units | 100 | 90.5 | 0 | 13.6 |
| | 15-18 weeks | | | |
| Protein | 17.5 | 17.20 | 17.5 | 16.24 |
| Fat | 8.68 | 8.00 | 9.78 | 9.21 |
| Calcium | 0.98 | 0.96 | 0.98 | 0.94 |
| T. Phosphorus | 0.65 | 0.68 | 0.65 | 0.70 |
| Hemicell units | 100 | 98.6 | 0 | 5.6 |
| | 18-20 weeks | | | |
| Protein | 16.0 | 15.95 | 16.0 | 15.14 |
| Fat | 9.14 | 8.93 | 10.29 | 10.39 |
| Calcium | 0.82 | 0.79 | 0.82 | 0.87 |
| T. Phosphorus | 0.57 | 0.61 | 0.57 | 0.65 |
| Hemicell units | 100 | 113.4 | 0 | 13.6 |

Glycoprotein Measurement:

Blood was obtained at the end of the trial from four birds per pen selected at random from treatments 1, 2, and 5. The blood was collected into tubes containing EDTA anticoagulant, mixed then centrifuged to precipitate the whole cells.

Turkey AGP test plates were obtained from Cardiotech Services (Louisville, Ky.). The AGP test is an immunodiffusion based test. Equal volumes of test or serum samples were added into the immunodiffusion plate wells as recommended by the manufacturer, then after two days incubation at room temperature, the diameter of the resulting immunoprecipitation rings was measured.

Figure 4:
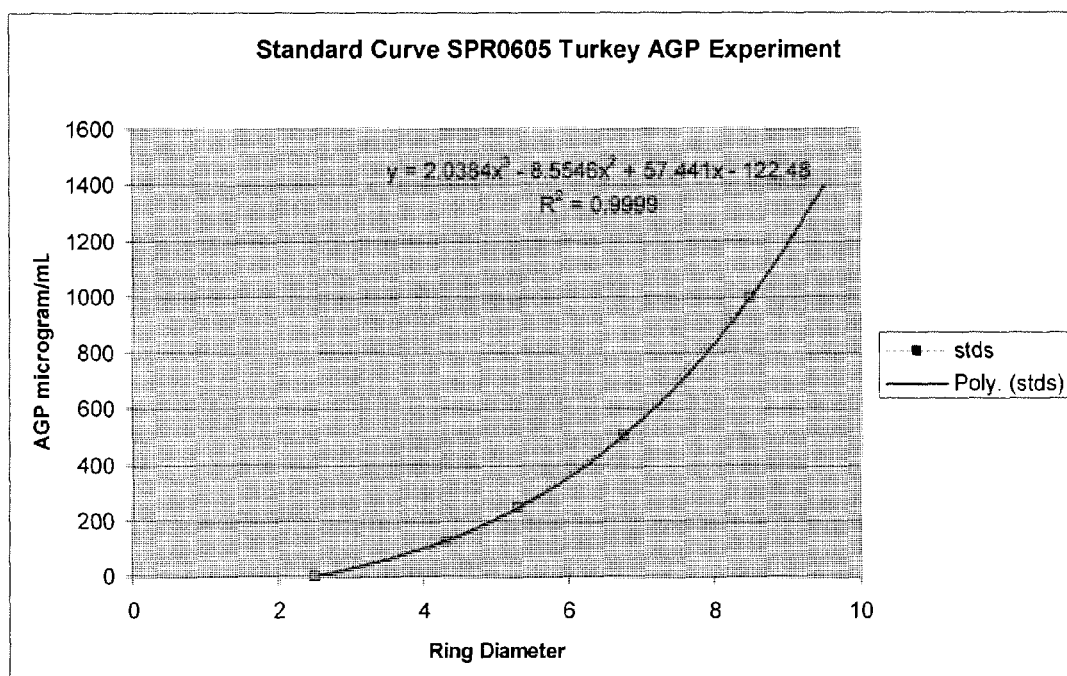
FIG. 4 shows the best curve fit (and underlying polynomial equation) for calculating the concentration of AGP in plasma samples of test turkeys with data obtained in Example 8.

A sample of purified turkey AGP standard provided in the kit was tested at several concentrations to make a standard curve as shown in FIG. 4. A polynomial curve fit equation developed from the standards was used to calculate the turkey plasma AGP level in the test samples.

Calculation of AGP Levels and Statistical Analysis with Students T Test

| Hemicell mannanase (Treatment 1) | | | Control (Treatment 2) | | |
|---|---|---|---|---|---|
| mm | AGP | outlier | mm | AGP | outlier |
| 5.2 | 231.5 | | 5.7 | 304.5 | |
| 4.8 | 181.6 | | 5.1 | 218.4 | |
| 5 | 205.7 | | 5.6 | 288.9 | |
| 5 | 205.7 | | 5.3 | 245.1 | |
| 5 | 205.7 | | 5.1 | 218.4 | |
| 5.1 | 218.4 | | 5.1 | 218.4 | |
| 5.3 | 245.1 | | 5.9 | 337.3 | |
| 6.1 | 372.3 | | 5 | 205.7 | |
| 5.8 | 320.6 | | 6.3 | 409.6 | |
| 4.7 | 170.2 | | 7.5 | | 687.1 |
| 4.9 | 193.4 | | 6.45 | 439.1 | |
| 5 | 205.7 | | 5.4 | 259.2 | |
| 5.2 | 231.5 | | 5.1 | 218.4 | |
| 5.5 | 273.8 | | 5.3 | 245.1 | |
| 5.7 | 304.5 | | 5.1 | 218.4 | |
| 5.1 | 218.4 | | 5.6 | 288.9 | |
| 4.7 | 170.2 | | 5.6 | 288.9 | |
| 5 | 205.7 | | 6.05 | 363.3 | |
| 4.5 | 148.5 | | 5.6 | 288.9 | |
| 5.3 | 245.1 | | 5.4 | 259.2 | |
| 5.2 | 231.5 | | 5 | 205.7 | |
| 4.4 | 138.3 | | 5 | 205.7 | |
| 4.3 | 128.4 | | 5.2 | 231.5 | |
| 6.35 | 419.3 | | 5.4 | 259.2 | |
| 4.9 | 193.4 | | 4.8 | 181.6 | |
| 5.65 | 296.6 | | 5 | 205.7 | |
| 5.2 | 231.5 | | 5.2 | 231.5 | |
| 5 | 205.7 | | 5.4 | 259.2 | |
| 4.8 | 181.6 | | 4.9 | 193.4 | |
| 5.2 | 231.5 | | 5.1 | 218.4 | |
| 7.5 | | 687.1 | 4.2 | 118.9 | |
| 5 | 205.7 | | 6.5 | 449.3 | |
| Ave | 226.4 | | | 260.5 | |
| Std. Deviation | 63.4 | | | 74.6 | |
| CV | 28.0 | | | 28.6 | |
| T Test P value | | | | 0.0284 | |

Outliers > 2 std. deviation from mean removed

The average plasma AGP for the enzyme treated group was significantly less than the untreated control. For this analysis, one outlier was removed from the analysis from each group. These may be birds that experienced an unusual amount of stress due to injury or infection. The reduced AGP caused by enzyme feeding was correlated with statistically significant improved live bird performance as shown below in Treatment 1 (mannanase) vs. Treatment 2.

140 Day Growth Results

| Pen | Weight | Mort. # | Mort. Weight | Feed Consumed | Feed Conv. | Live Wt. Gain | CV in weight 140 d |
|---|---|---|---|---|---|---|---|
| | | | | Hemicell | | | |
| 3 | 200.25 | 0 | 0 | 487.35 | 2.434 | 18.147 | 5.766 |
| 7 | 193.3 | 0 | 0 | 479.55 | 2.481 | 17.512 | 7.426 |
| 14 | 143.95 | 3 | 10.817 | 389.05 | 2.514 | 17.934 | 6.857 |
| 21 | 164.1 | 2 | 24.205 | 448.70 | 2.383 | 18.172 | 4.411 |
| 29 | 185.8 | 1 | 0.975 | 448.90 | 2.403 | 18.521 | 6.092 |
| 36 | 161.1 | 2 | 16.49 | 419.90 | 2.364 | 17.839 | 8.352 |
| 37 | 182.1 | 1 | 7.611 | 443.70 | 2.339 | 18.150 | 5.944 |
| 47 | 182.55 | 1 | 13.115 | 449.05 | 2.295 | 18.195 | 3.405 |
| Avg. | | | | 445.78 | 2.402 | 18.059 | 6.032 |
| T Test Vs. Trt 2 | | P val | | | 0.05 | 0.01 | 0.05 |

-continued

| Pen | Weight | Mort. # | Mort. Weight | Feed Consumed | Feed Conv. | Live Wt. Gain | CV in weight 140 d |
|---|---|---|---|---|---|---|---|
| | | | Control | | | | |
| 5 | 144.1 | 2 | 13.085 | 389.00 | 2.475 | 15.950 | 14.518 |
| 12 | 196.1 | 0 | 0 | 486.70 | 2.482 | 17.766 | 5.288 |
| 13 | 178.7 | 1 | 14.65 | 466.25 | 2.411 | 17.810 | 9.717 |
| 23 | 141.95 | 3 | 21.912 | 389.40 | 2.376 | 17.684 | 8.012 |
| 28 | 190.2 | 0 | 0 | 482.10 | 2.535 | 17.231 | 9.331 |
| 35 | 194.5 | 0 | 0 | 486.25 | 2.500 | 17.622 | 9.722 |
| 42 | 159.25 | 2 | 10.814 | 409.40 | 2.407 | 17.635 | 5.054 |
| 48 | 176.65 | 1 | 9.05 | 459.10 | 2.472 | 17.605 | 4.772 |
| | Avg. | | | 446.03 | 2.457 | 17.413 | 8.302 |

Birds receiving feed with mannanase had greater average weight gain by 3.7%, decreased feed conversion by 2.3% and decrease in the CV (coefficient of variation=std. deviation/mean) of body weight uniformity. The reduction in immune stress as indicated by reduced AGP serum levels correlated with several measurements of growth improvement.

EXAMPLE 9

In this example 1,413-mannanase from *B. lentus*, 1,3-β-glucanase from *B. lentus*, and a combination of the two enzymes were added to feed (a conventional corn-soybean diet). Each enzyme treatment improved live growth performance in 6 week old Nicholas 700 female turkeys, with results achieved by the combination being unexpectedly greater than results achieved with treatments using only one of the enzymes.

The experiment used 80 pens of 40 female turkeys. The treatments were replicated in ten (10) blocks, with eight treatments (seven enzyme treatments and one negative control) randomized within each block.

Treatment 3 used a composition comprising an immune stress-reducing enzyme in accordance with the invention, 1,4-β-mannanase at 100 MU/ton of feed. Treatment 6 also used a composition comprising an immune stress-reducing enzyme in accordance with the invention, 1,3-β-glucanase at 60 MU/ton of feed. Treatment 8 used a combination composition in accordance with the invention, comprising 1,4-β-mannanase at 100 MU/ton of feed and 1,3-β-glucanase at 60 MU/ton of feed. Treatment 1 was a control feed without added enzyme. (1 MU=4000 IU)

Feed was mixed to assure uniform distribution of basal feeds among treatments. All enzymes were mixed (sprayed on) to assure a uniform distribution of test enzymes and to assure similar feed condition between treatments. Each time a treatment feed was made, a sample from the beginning, middle, and end of each treatment feed were mixed to fowl a composite sample. One sample was taken from the composite for each treatment, and for enzyme level verification.

The turkey diets fed in this study are typical commercial turkey feeds. The diets are representative of what might be used in a commercial turkey growing operation and thus the diet was adjusted after 3 weeks. The growth results for Treatments 1, 3, 6 and 8 are shown in the table below.

| | 6-week Growth Parameters | | | |
|---|---|---|---|---|
| Treatment | Mortality (%) | Average Live Weight (lbs) | Feed Conversion[1] | Weight-Adjusted Feed Conversion[2] |
| T1 Control | 1.75[A] | 5.406[A] | 1.500[A] | 1.520[A] |
| T3 1,4-β-mannanase (100 MU/ton) | 1.50[A] | 5.484[ABC] | 1.495[AB] | 1.502[AB] |
| T6 1,3-β-glucanase (60 MU/ton) | 1.50[A] | 5.540[C] | 1.467[C] | 1.465[C] |
| T8 1,4-β-mannanase (100 MU/ton) and 1,3-β-glucanase (60 MU/ton) | 3.25[A] | 5.718[D] | 1.420[D] | 1.389[D] |

(1 MU = 4000 IU)
Note 1:
Feed Conversion is mortality corrected.
Note 2:
Weight-adjusted feed conversion for each treatment is calculated as follows: (a) the average live weight of the entire test is subtracted from the average live weight for the treatment, resulting in Quantity A; (b) Quantity A is divided by 6, resulting in Quantity B; (c) Quantity B is subtracted from the feed conversion resulting in the weight-adjusted feed conversion for the treatment. Statistics shown are for LSD test; $P < 0.05$.

In comparison to Treatment 1 (control), Turkey hens receiving Treatment 3 (feed with 1,4-β-mannanase) had a numerically improved average live weight and a numerically improved (decreased) feed conversion. Similarly, Turkey hens receiving Treatment 6 (feed with 1,3-β-glucanase) had a statistically-significant improved average live weight and a statistically-significant improved (decreased) feed conversion.

Surprisingly, Turkey hens receiving Treatment 8 (feed with a combination of 1,4-β-mannanase and 1,3-β-glucanase) had an unusually large statistically significant improved average live weight and an unusually large statistically significant improved (decreased) feed conversion. The results observed with Treatment 8 were greater than could be explained by an additive effect of the two enzymes administered individually. Thus, the combination treatment comprising 1,4-β-mannanase and 1,3-β-glucanase produced an unexpectedly large improvement in growth performance.

EXAMPLE 10

In this example, 1,3-β-glucanase from *B. lentus*, xyloglucanase from *B. lentus* and a combination of the two enzymes were added to feed (a conventional corn-soybean diet). Each enzyme treatment improved live growth performance in 35-day old male broiler chickens, with results achieved by the combination being greater than results achieved with treatments using only one of the enzymes.

The experiment used 49 pens of 44 Cobb×Cobb male chickens. The treatments were replicated in seven blocks, with seven treatments (six enzyme treatments and one negative control) randomized within each block.

Treatment 4 used a composition comprising an immune stress-reducing enzyme in accordance with the invention, 1,3-β-glucanase at 70 MU/ton of feed. Treatment 5 also used a composition comprising an immune stress-reducing enzyme in accordance with the invention, xyloglucanase at 100 MU/ton of feed. Treatment 6 used a combination composition in accordance with the invention, comprising xyloglucanase at 100 MU/ton of feed and 1,3-β-glucanase at 60 MU/ton of feed. Treatment 1 was a control feed without added enzyme. (1 MU=4000 IU).

Feed was mixed to assure uniform distribution of basal feeds among treatments. All enzymes were mixed (sprayed on) to assure a uniform distribution of test enzymes and to assure similar feed condition between treatments. Each time a treatment feed was made, a sample from the beginning, middle, and end of each treatment feed were mixed to form a composite sample. One sample was taken from the composite for each treatment, and for enzyme level verification.

The diets fed in this study are typical broiler chicken feeds. The diets are representative of what might be used in a commercial broiler growing operation and thus the diet was adjusted after 3 weeks. The growth results for Treatments 1, 4, 5, and 6 after 35 days of growth are shown in the table below:

| | 35-day Growth Parameters | | | |
|---|---|---|---|---|
| Treatment | Mortality (%) | Average Live Weight (lbs) | Feed Conversion[1] | Weight-Adjusted Feed Conversion[2] |
| T1 Control | 3.25$^A$ | 4.347$^A$ | 1.675$^A$ | 1.690$^A$ |
| T4 1,3-β-glucanase (70 MU/ton) | 3.25$^A$ | 4.433$^{AB}$ | 1.651$^{AB}$ | 1.651$^{AB}$ |
| T5 Xyloglucanase (100 MU/ton) | 2.92$^A$ | 4.415$^{AB}$ | 1.646$^{AB}$ | 1.650$^{AB}$ |
| T6 Xyloglucanase (100 MU/ton) And 1,3-β-glucanase (70 MU/ton) | 4.55$^A$ | 4.461$^{AB}$ | 1.643$^{AB}$ | 1.639$^{AB}$ |

(1 MU = 4000 IU)
Note 1:
Feed Conversion is mortality corrected.
Note 2:
Weight-adjusted feed conversion for each treatment is calculated as described above. Statistics shown are for LSD test; $P < 0.05$.

In comparison to Treatment 1 (control), the chickens receiving Treatment 4 (1,3-β-glucanase) had a numerically improved average live weight and a numerically improved (decreased) feed conversion. Similarly, the chickens receiving Treatment 5 (feed with xyloglucanase) had a numerically improved average live weight and a numerically improved (decreased) feed conversion.

Chickens receiving Treatment 6 (a combination of 1,3-β-glucanase and xyloglucanase) achieved improvements in their average live weight and feed conversions greater than the effect observed when the enzymes were administered individually. Thus, the combination treatment comprising 1,3-β-glucanase and xyloglucanase achieved a significant improvement in growth performance.

EXAMPLE 11

Reduction of Chicken Serum APP by Application of Enzymes in Feed

Chicken broilers were grown from 1 to 14 days and fed a typical corn-soybean starter diet (as shown in the Diet Composition table below) with various enzymes added (as summarized in the Enzyme table below). Sample sizes for each enzyme type included three cages with eight birds per cage.

Diet Composition

| Component | Percent |
|---|---|
| Corn 7.35% CP | 53.98 |
| Soybean meal 47.2 CP | 39.03 |
| Soy oil | 3.0 |
| Limestone | 1.307 |
| Dicalcium phosphate | 1.735 |
| Salt (NaCl) | 0.331 |

-continued

| Component | Percent |
|---|---|
| DL Methionine | 0.186 |
| Vitamin premix | 0.25 |
| Choline chloride 60% | 0.05 |
| Copper Sulfate | 0.05 |

Enzymes

| Treatment | Enzyme 1 | Enzyme 2 | Enzyme 3 | mG/L AGP | P val T Test |
|---|---|---|---|---|---|
| A | — | — | — | 268.1 | |
| B | 1,3-β-galactanase (46,495 IU/ton) | 1,4-β-mannanase (85,312 IU/ton) | — | 281.4 | |
| C | 1,3-β-galactanase (9,8911 IU/ton) | 1,4-β-mannanase (181,488 IU/ton) | — | 266.6 | |
| D | 1,4-β-galactanase (81,046 IU/ton) | 1,4-β-mannanase (174,889 IU/ton) | — | 261.7 | |
| E | 1,4-β-galactanase (114,418 IU/ton) | 1,4-β-mannanase (246,902 IU/ton) | — | 261.7 | |
| F | xylanase (95,225 IU/ton) | 1,4-β-mannanase (381,142 IU/ton) | — | 257.8 | |
| G | chitinase (5,218 IU/ton) | 1,4-β-mannanase (27,016 IU/ton) | — | 263.8 | |
| H | chitinase (5,218 IU/ton) | 1,4-β-mannanase (205,807 IU/ton) | — | 220.2 | 0.040 |
| I | 1,3-β-glucanase (127,042 IU/ton) | 1,4-β-mannanase (181,488 IU/ton) | — | 236.9 | 0.125 |
| J | xylanase (126,758 IU/ton) | 1,4-β-mannanase (362,976 IU/ton) | esterase | 234.5 | 0.083 |

The "esterase" in Treatment J is an uncharacterized enzyme from a *B. lentus* gene in the same operon with xylanase. The substrate for this enzyme was not identified. Its assignment as an "esterase" is based on the similarity of the DNA sequence of this gene to other known esterase genes. The esterase activity was not determined, but would be similar to the xylanase level if the two proteins have similar specific activities.

The 1,4-β-galactanase and 1,3-galactanase were measured using a reducing sugar assay with pectin substrate.

At 14 days, blood serum was collected from all birds and samples were analyzed for α1-acid glycoprotein (AGP) content as described above. The average level of α-1-acid glycoprotein from each treatment group is shown in the table above.

As reflected in the table, relative to Treatment A (no enzyme), Treatments H, I and J resulted in reduction of serum AGP.

Treatment H (chitinase plus 1,4-β-mannanase) yielded significant results after only two weeks of growth. Although the amounts of enzymes were at levels that did not show a response in other Treatments (compare to Treatment G with a comparable amount of chitinase and Treatments E and F with a comparable amounts of 1,4-β-mannanase), the combination of chitinase and 1,4-β-mannanase resulted in significant AGP reduction, that could not be predicted from the results obtained when only one enzyme was used.

Treatment I (1,3-β-glucanase and 1,4-β-mannanase) yielded notable results, although not clearly statistically significant in this experiment (P value of 0.125). In other tests of longer duration, treatment with 1,3-β-glucanase and 1,4-β-mannanase did have a significant effect on AGP level.

Comparing Treatment J (xylanase, 1,4-β-mannanase, esterase; P=0.083 vs Treatment A control) to Treatment F (xylanase+1,4-β-mannanase, without "esterase") reveals that Treatment J yielded a notable effect, where Treatment F did not show AGP reduction.

EXAMPLE 12

This example tests the hypothesis that altering a feed composition to include ingredients that stimulate the innate immune system will increase serum APP levels.

A 21-day chicken broiler test was performed using a basal corn-soybean diet with a soy-oil high-energy diet as control. To obtain test diets, the control diet was modified to contain practical materials suspected to have immune stimulatory components while maintaining the same approximate equivalent nutritional value. The test diets included the following variations:

Corn/soy/soy oil control
AV blend oil (animal vegetable blend oil) inclusion;
soy lecithin inclusion;
poultry meal inclusion;
DDGS (distillers grains and solubles by-product from ethanol manufacture) inclusion at 5% with soy hull;
DDGS inclusion at 15% w/o soy hull.

The diets are described in more detail in the tables below.

The AV blend and soy lecithin are expected to contain phospholipids comprising the innate immune system stimulator phosphatidylserine. The poultry meal may contain phosphatidylserine, hyaluronan, and various microbial stimulators derived from the offal or secondary microbial growth that could occur before processing. The DDGS is expected to contain abundant yeast residue, including cell walls comprising α-mannan, 1,3-β-glucan and chitin, as well as potentially stimulating non-fermented carbohydrate polymers from the original fermentation substrate.

Diet Compositions

For each diet, chicken broilers (Cobb×Cobb) were grown in three Petersime battery cages with eight birds per cage (0.631 sq. ft. per bird). After 21 days, the serum AGP levels of each bird was analyzed as described in previous examples.

The modified diets showed clear evidence of innate immune system stimulation based on significant increases in serum AGP at 21 days, as shown in the following table. The data also underscores the opportunities to reduce immune stress caused by diet components in accordance with the invention, such as by the use of compositions comprising enzymes that degrade immune stress inducing ingredients.

| Diet | Addition | Mg/L AGP | T Test (P value vs. 1) |
|---|---|---|---|
| 1 | Control | 221.9 | |
| 2 | AV blend | 301.2 | 0.01882 |
| 3 | Lecithin | 309.0 | 0.01052 |
| 4 | Poultry Meal | 265.8 | 0.08613 |
| 5 | DDGS w/hull | 307.6 | 0.00002 |
| 6 | DDGS | 386.7 | 0.00275 |

EXAMPLE 13

This example demonstrates the efficacy of compositions comprising 1,3-β-glucanase in reducing immune stress associated with 1,3-β-glucan, which is present in feedstuffs and, by virtue of its association with fungal cell walls, is a molecular pattern apparently recognized universally by the innate immune system of animals. The results show that, like 1,4-β-mannanase, 1,3-β-glucanase reduces serum levels of APP and improves animal growth performance.

Chicken broilers (Cobb×Cobb) were grown from day 1 to 21 on the typical low fat corn/soybean meal diet shown in the

| | Percent Composition | | | | | |
|---|---|---|---|---|---|---|
| Component | Diet #1 | Diet #2 | Diet #3 | Diet #4 | Diet #5 | Diet 6 |
| Corn 7.35% CP | 56.9707 | 56.2985 | 56.2985 | 59.878 | 47.7939 | 49.3523 |
| Soy meal 48.5% CP | 36.4392 | 36.5403 | 36.5403 | 29.048 | 29.0293 | 29.0284 |
| Soy oil | 2.5279 | 0 | 0 | 1.7221 | 3.1922 | 2.6831 |
| AV blend | 0 | 3.0975 | 0 | 0 | 0 | 0 |
| Soy lecithin | 0 | 0 | 3.0975 | 0 | 0 | 0 |
| Poultry BPM[a] 65% | 0 | 0 | 0 | 5.0 | 0 | 0 |
| Soy hulls[d] | 0 | 0 | 0 | 1.0559 | 1.0586 | 0 |
| DDGS[b] | 0 | 0 | 0 | 0 | 15 | 15 |
| Limestone | 1.3129 | 1.3118 | 1.3118 | 1.2224 | 1.4158 | 1.4293 |
| Dicalcium phosphate | 1.7527 | 1.7544 | 1.7544 | 1.766 | 1.5615 | 1.5576 |
| Salt | 0.3312 | 0.3315 | 0.3315 | 0.2313 | 0.1416 | 0.1407 |
| DL-methionine | 0.2404 | 0.241 | 0.241 | 0.2276 | 0.2419 | 0.2392 |
| L-lysine HCl | 0 | 0 | 0 | 0.0131 | 0.1402 | 0.1402 |
| Vitamin premix 0.25% | 0.25 | 0.25 | 0.25 | 0.25 | 0.25 | 0.25 |
| Mineral PMX 0.075% | 0.075 | 0.075 | 0.075 | 0.075 | 0.075 | 0.075 |
| Choline chloride 60% | 0.05 | 0.05 | 0.05 | 0.05 | 0.05 | 0.05 |
| Copper sulfate | 0.05 | 0.05 | 0.05 | 0.05 | 0.05 | 0.05 |

[a] poultry BPM (by product meal);
[b] DDGS (distiller dry grain and solubles);
[c] AV blend (animal vegetable blend oil);
[d] addition of soy hulls to the poultry meal diet equalizes the mannan content to compensate for reduced soy meal table below. In two cases, the diets were supplemented by uniformly spraying liquid enzyme concentrate solutions prepared from *B. lentus* fermentations to apply either 400,000 IU/ton 1,4-β-mannanase or 264,000 IU/ton 1,3-β-glucanase. (In this case, a ton represents 2000 lbs. or 907.4 kg.)

Diet Composition

| Component | Diet % |
| --- | --- |
| Corn 7.35% CP | 59.5757 |
| Soy meal 48.5% CP | 36.0474 |
| Soy oil | 0.321 |
| Limestone | 1.3175 |
| Dicalcium phosphate | 1.7461 |
| Salt | 0.3294 |
| DL-methionine | 0.2378 |
| Vitamin premix 0.25% | 0.25 |
| Mineral PMX 0.075% | 0.075 |
| Choline chloride 60% | 0.05 |
| Copper sulfate | 0.05 |

For each diet type, birds were grown in three Petersime® battery cages with eight birds per cage (0.631 sq. ft. per bird). After 21 days, serum AGP levels of each bird was analyzed as described in previous examples. Bird weights and feed consumed were determined utilizing standard procedures and feed conversion was calculated. The results are shown in the following table WAFC (weight adjusted feed conversion) is calculated as follows:

$$WAFC = FC - 2.204 * ((W - Wa)/3)$$

where

FC=weight of feed consumed/weight gained
Wa=average weight of all birds in the trial
W=average live weight gain per cage

| Treatment | mg/L AGP | T Test P vs. contr. | WAFC | P value |
| --- | --- | --- | --- | --- |
| Control (no enzyme) | 255.4 | | 1.47 | a |
| 1,4-β-mannanase | 184.1 | 0.011 | 1.39 | ab |
| 1,3-β-glucanase | 157.7 | 0.001 | 1.26 | c |

Both 1,4-β-mannanase and 1,3-β-glucanase reduced the serum levels of α1-acid glycoprotein (AGP). Both enzyme treatments reduced the weight adjusted feed conversion, and the reduction in the 1,3-β-glucanase fed group was statistically significant.

EXAMPLE 14

A chicken broiler trial was conducted in Petersine® battery cages with the feed and methods described in Example 13 above, except with different enzyme treatments, as summarized in the table below.

Lyticase, a crude 1,3-β-glucanase product obtained by fermentation of *Arthrobacter luteus*, was obtained from the Sigma Chemical Company, St. Louis Mo. Lyticase activity was determined by the reducing sugar method described below and 60 MU/ton (equivalent to 240,000 IU/ton) was applied. According to the manufacturer, this product also contains other activities, including chitinase activity, that was not measured.

| Treatment | Enzyme(s) | Dose (MU/ton) | AGP (mg/L) |
| --- | --- | --- | --- |
| 1 | none | 0 | 215.5 |
| 2 | 1,3-β-glucanase | 3 | 213.7 |
| 3 | 1,3-β-glucanase | 15 | 199.4 |
| 4 | 1,3-β-glucanase | 30 | 185.5 |
| 5 | 1,3-β-glucanase | 60 | 201.0 |
| 6 | 1,3-β-glucanase 1,4-β-mannanase | 60 100 | 189.2 |
| 7 | 1,3-β-glucanase | 75 | 194.9 |
| 8 | 1,3-β-glucanase | 90 | 180.7 |
| 9 | Lyticase | 60 | 165.2 |
| 10 | Xyloglucanase | 100 | 162.2 |

(1 MU = 4000 IU)

Increased levels of 1,3-β-glucanase resulted in an increased effect on AGP level (e.g., a dose response) up to about 30 MU/ton (120,000 IU/ton). Providing this type of animal feed with about 30 MU/ton (120,000 IU/ton) 1,3-β-glucanase is expected to reduce immune stress, as reflected in a reduced level of serum AGP and/or improved animal growth performance.

The results also show that xyloglucanase was effective at reducing serum AGP levels. Xyloglucanase (EC 3.2.1.151) is a 1,4-β-glucanase with specificity for xyloglucan, a structural polymer in plants.

With the exception of the Lyticase, all of the enzymes used in this example were produced by *B. lentus*. Lyticase is produced by *A. luteus* which has been reclassified as *Cellulosimicrobium cellulans*. Fermentation of *A. luteus* has been shown to produce multiple forms of 1,3-β-glucanase. See, e.g., (Ferrer, P. *Microb Cell Factories* 5:10, 2006, published online 2006 Mar. 17. doi: 10.1186/1475-2859-5-10). The results above show that Lyticase reduced the chicken serum AGP at least as well as the *B. lentus* 1,3-β-glucanase preparation, indicating that the source of the enzyme is not important. That is, enzymes from any source can be used in accordance with the invention. It also is possible that chitinase (reported by Sigma to be present in Lyticase) may have improved the performance of the Lyticase treatment.

EXAMPLE 15

The following assays can be used to assess enzyme activity (I) Xyloglucanase

Xyloglucanase activity can be assayed using the following protocol:

DNS Reagent:

10 g/L NaOH, 2 g/L phenol, 10 g/L dinitrosalicylic acid, 1200 g/L potassium sodium tartrate tetrahydrate is prepared daily. Immediately before use, 0.5 g/L anhydrous sodium sulfite is added.

Standard Solutions and Standard Curve:

A series of D-(+)-mannose standard solutions dissolved in water in the concentration range of 0.1 to 0.5 g/Liter are prepared. 0.6 mL of each mannose standard (in duplicate or triplicate) is added to 1.5 mL DNS working solution in 13×100 mm glass tubes. A sample with a 0.6 mL aliquot of water can be used as a reagent blank to zero the spectrophotometer. The solutions are heated in a boiling water bath for 5 minutes, cooled to ambient temperature and absorbance is read at 550 nm. The expected result is a linear dose response between 0.20 and 1.2 O.D. units. The slope of the standard curve (O.D 550/g/L mannose) is calculated from the linear portion of the curve only. With this slope, the value of the g/L of reducing sugar is determined in the enzyme reactions.

Xyloglucan Substrate:

Xyloglucan (Tamarind) is obtained from Megazyme International Ireland Ltd., Bray, Co., Ireland is dissolved at 5 g/L in 50 mM Tris buffer, pH 7.5 with 0.05% glucose.

Reaction Conditions:

0.25 mL of 5 g/L xyloglucan substrate is used with a 0.05 mL enzyme dilution in 50 mM Tris buffer, and the reaction mixture is incubated at 40° C. 0.75 mL DNS reagent is added to stop the reaction, and the stopped reaction mixture is heated in boiling water bath for five minutes and then cooled prior to reading absorbance at 550 nm. A zero time point with enzyme solution is used to determine the background level.

Calculation:

A ChemGen xyloglucanase MU is defined as the ability to produce 0.72 grams of reducing sugar per minute (using pure mannose, a reducing sugar, as standard). One ChemGen MU is equivalent to 4000 IU. In other words, one CG U is equivalent to 250 IU (IU=1.0µ mole/minute).

(II) B-1,3-glucanase

B-1,3-glucanase activity can be assayed using the following protocol:

This assay uses the same DNS reagent, standard solutions, standard curve, and enzyme unit calculation and dilution amount as described above for the xyloglucanase assay. The buffer used is a 50 mM MOPS (4-Morpholinepropanesulfonic Acid, FW=209.26) buffer at pH 6.5.

CM Pachyman Substrate:

Carboxymethyl Pachyman (CM Pachyman, CMP) is obtained from Megazyme International Ireland Ltd., Bray, Co., Ireland. CMP substrate is prepared at 5 g/L by slowly adding CMP into a fast stirring 50 mM MOPS buffer solution (pH 6.5) at about 90° C. The enzyme powder is well-dispersed, and the vessel is covered or sealed tightly, while the suspension is heated slowly to boiling and simmered for 30 minutes with stirring on a heated—stir plate, to obtain a well-hydrated gel with no small clumps of non-hydrated gel visible in the solution. The solution is cooled to room temperature, stored at 4° C. when not in use, and mixed well prior to use after storage.

Reaction Conditions:

0.25 mL of 5 gL CM Pachyman substrate is used with 0.05 mL enzyme dilution in MOPS buffer and the reaction mixture is incubated at 40° C. for various times, up to 45 minutes. 0.75 mL DNS reagent is added to stop the reaction. The stopped reaction mixture is heated in boiling water bath for five minutes and then cooled prior to reading absorbance at 550 nm. A zero time point with enzyme solution is used to determine the background level.

(III) Chitinase

Chitinase activity can be determined using the fluorogenic chitin substrate described in Thompson et al., Appl. Environ. Microbiol. 67: 4001-008 (2001), 4-methylumbelliferyl-beta-D-N,N',N'',N'''-tetraacetylchitotetraoside. The substrate is dissolved in DMSO at 2.5 mM.

In an exemplary assay, 20 µL chitin substrate (2.5 mM) is used with 150 µL tris (20.0 mM, pH 7.5). The substrate mixture is placed in a black 98 well microtiter plate and pre-heated to 37° C. for 10 minutes. Multiple replicaes of reactions are started by addition of 30 µL diluted enzyme and incubation is continued at 37° C. Individual reactions are stopped at 2, 4, 6, 8 and 10 minutes with 50 µL 3 $MNa_2CaO_3$. Fluorescence is read in a microtiter plate reader (Fluoroscan II) using excitation 355 nm band pass filter and emission 460 nm band pass filter wavelengths. The enzyme is diluted such that the 4-methylumbelliferone is produced at a linear rate for the term of the reaction and within the range of a standard curve produced under conditions identical to the enzyme assay but without enzyme and substrate present. The release of one micromole of 4-methylumbelliferone per minute is defined as one IU. A standard curve is made with several concentrations between zero and $1 \times 10^{-4}$ micromole 4-methylumbelliferone in 200 µL reaction buffer solution followed by addition of 50 µL 3 $MNa_2CaO_3$.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

What is claimed is:

1. A composition suitable for oral administration to an animal comprising an immune stress-reducing enzyme in an orally acceptable carrier, wherein said composition is selected from the group consisting of:
   (i) an animal/feed comprising at least 20 IU of said immune stress-reducing enzyme/kg feed;
   (ii) a liquid composition other than an animal feed comprising at least 40,000 IU of said immune stress-reducing enzyme/L; and
   (iii) a solid composition other than an animal feed comprising at least 40,000 IU of said immune stress-reducing enzyme/kg,
   wherein said immune stress-reducing enzyme is selected from the group consisting of α-1,6-mannosidase, α-1,2-mannosidase, α-1,3-mannosidase, and endo-α-1,6-D-mannanase.

2. The composition of claim 1, wherein said composition is an animal feed comprising at least 20 of said immune stress-reducing enzyme/kg feed.

3. The composition of claim 1, wherein said composition is a liquid composition other than an animal feed comprising at least 40,000:EU of said immune stress-reducing enzyme/L.

4. The composition of claim 1, wherein said composition is a solid composition other than an animal feed comprising at least 40,000 IU of said immune stress-reducing enzyme/kg.

5. The composition of claim 1, wherein the composition is a solid composition other than an animal feed comprising at least 80,000 TU of said immune stress-reducing enzyme/kg.

6. The composition of claim 1, wherein the composition is a solid composition other than an animal feed comprising at least 160,000 IU of said immune stress-reducing enzyme/kg.

7. The composition of claim 1, wherein the composition is an animal feed that comprises an ingredient that induces an immune response in the animal and wherein said immune stress-reducing enzyme degrades said ingredient.

8. The composition of claim 7, wherein said ingredient is a non-pathogenic molecule that displays a molecular pattern that is recognized by the animal's innate immune system, and that is degraded by said immune stress reducing enzyme.

9. The composition of claim 7, wherein said ingredient is an antigen displayed by a pathogenic microorganism.

10. A method of improving animal growth performance and/or reducing immune stress in an animal, comprising orally administering to said animal a composition according to claim 1.

11. The method of claim 10, wherein said animal is administered an ingredient that induces an immune response in the animal and wherein said immune stress reducing enzyme degrades said ingredient.

12. The method of claim 11, wherein said ingredient and said immune stress-reducing enzyme are administered in the same composition.

13. The method of claim 12, wherein said composition is an animal feed.

14. The method of claim 11, wherein said ingredient is a non-pathogenic molecule that displays a molecular pattern that is recognized by the animal's innate immune system, and that is degraded by said immune stress reducing enzyme.

15. The method of claim 11, wherein said ingredient is an antigen displayed by a pathogenic microorganism.

16. A method of preventing or treating infection associated with a pathogenic microorganism that displays an antigen, comprising orally administering to an animal in need thereof a composition according to claim 1, wherein said immune stress-reducing enzyme degrades said antigen.

* * * * *

UNITED STATES PATENT AND TRADEMARK OFFICE
CERTIFICATE OF CORRECTION

PATENT NO. : 8,778,648 B2
APPLICATION NO. : 13/072123
DATED : July 15, 2014
INVENTOR(S) : Anderson et al.

It is certified that error appears in the above-identified patent and that said Letters Patent is hereby corrected as shown below:

On the Title Page item [56], Column 2, Line 36, please delete "off" and insert -- of --, therefor.

In the Claims

Column 40, Line 33, Claim 1, please delete "animal/fee" and insert -- animal feed --, therefor.

Column 40, Line 46, Claim 2, please delete "20" and insert -- 20 IU --, therefor.

Column 40, Line 50, Claim 3, please delete "40,000:EU" and insert -- 40,000 IU --, therefor.

Column 40, Line 56, Claim 5, please delete "80,000 TU" and insert -- 80,000 IU --, therefor.

Column 41, Line 9, Claim 11, please delete "stress reducing" and insert -- stress-reducing --, therefor.

Signed and Sealed this
Twenty-eighth Day of October, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,778,648 B2 | Page 1 of 1 |
| APPLICATION NO. | : 13/072123 | |
| DATED | : July 15, 2014 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 544 days.

Signed and Sealed this
First Day of December, 2015

Michelle K. Lee
*Director of the United States Patent and Trademark Office*